United States Patent
Gazzaley

(10) Patent No.: US 11,049,408 B2
(45) Date of Patent: *Jun. 29, 2021

(54) ENHANCING COGNITION IN THE PRESENCE OF DISTRACTION AND/OR INTERRUPTION

(71) Applicant: THE REGENTS OF THE UNIVERSITY OF CALIFORNIA, Oakland, CA (US)

(72) Inventor: Adam Gazzaley, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 286 days.

This patent is subject to a terminal disclaimer.

(21) Appl. No.: 15/787,386

(22) Filed: Oct. 18, 2017

(65) Prior Publication Data

US 2018/0261115 A1 Sep. 13, 2018

Related U.S. Application Data

(63) Continuation of application No. 13/879,589, filed as application No. PCT/US2011/060260 on Nov. 10, 2011, now Pat. No. 9,940,844.

(Continued)

(30) Foreign Application Priority Data

Nov. 12, 2010 (CA) .................................. CA 2720892

(51) Int. Cl.
*G09B 5/02* (2006.01)
*A61B 5/16* (2006.01)
(Continued)

(52) U.S. Cl.
CPC ................ *G09B 5/02* (2013.01); *A61B 5/162* (2013.01); *A61B 5/168* (2013.01); *A61B 5/4884* (2013.01); *G09B 7/02* (2013.01); *H04L 67/10* (2013.01)

(58) Field of Classification Search
CPC ....................................................... G09B 5/02
See application file for complete search history.

(56) References Cited

U.S. PATENT DOCUMENTS 4,028,819 A * 6/1977 Walker ..................... A61B 5/16
434/258
4,730,253 A * 3/1988 Gordon ................... A61B 5/168
273/429

(Continued)

FOREIGN PATENT DOCUMENTS

JP 200513713 1/2005
JP 2007292908 11/2007

(Continued)

OTHER PUBLICATIONS

Anguera et al. (2010) "Age-Related Changes in Distraction & Multitasking during a Driving Video Game" Department of Neurology and Physiology, W.M. Keck Center for Integrative Neurosciences, University of California San Francisco, San Francisco, California. Nov. 16, 2010. Poster.

(Continued)

*Primary Examiner* — Xuan M Thai
*Assistant Examiner* — Sadaruz Zaman
(74) *Attorney, Agent, or Firm* — Brian E. Davy; Bozicevic, Field & Francis LLP

(57) ABSTRACT

The present disclosure relates to methods and tools for enhancing cognition and improving well being in an individual. The methods involve presenting to an individual a task to be performed, presenting to the individual an interference, and receiving inputs from the individual. Where the (Continued)

interference is a distraction, the individual is to ignore the interference. Where the interference is an interruptor, the individual is instructed to respond to the interrupter as a secondary task and is said to be multi-tasking. Inputs are then also received from the individual pertaining to this secondary task. The methods encompass iterations of these presenting steps and receiving of the input, and generation of analysis and/or feedback to the individual. The methods can further include conducting an analysis and/or generating feedback to the individual. The analysis can include a comparison of the performances with or without each type of interference.

24 Claims, 12 Drawing Sheets

Related U.S. Application Data

(60) Provisional application No. 61/412,738, filed on Nov. 11, 2010.

(51) Int. Cl.
*H04L 29/08* (2006.01)
*A61B 5/00* (2006.01)
*G09B 7/02* (2006.01)

(56) References Cited

U.S. PATENT DOCUMENTS

| | | | |
|---|---|---|---|
| 5,137,027 A | 8/1992 | Rosenfeld | |
| 5,303,327 A | 4/1994 | Sturner | |
| 5,363,858 A | 11/1994 | Farwell | |
| 5,762,611 A | 6/1998 | Lewis | |
| 6,186,145 B1 | 2/2001 | Brown | |
| 6,261,101 B1 | 7/2001 | Benitz et al. | |
| 6,290,504 B1 | 9/2001 | Benitz et al. | |
| 6,413,098 B1 | 7/2002 | Tallel et al. | |
| 6,549,752 B2 | 4/2003 | Tsukamoto | |
| 6,632,174 B1 | 10/2003 | Breznitz | |
| 6,746,409 B2 | 6/2004 | Keirsbilck | |
| 6,832,110 B2 | 12/2004 | Sohmer | |
| 6,840,908 B2 | 1/2005 | Edwards et al. | |
| 7,384,399 B2 | 6/2008 | Ghajar | |
| 7,540,615 B2 | 6/2009 | Merzenich et al. | |
| 7,774,052 B2 | 8/2010 | Burton | |
| 7,942,828 B2 * | 5/2011 | Teicher | A61B 5/168 600/558 |
| 8,029,138 B2 | 10/2011 | Todd | |
| 8,231,543 B2 | 7/2012 | Benasich et al. | |
| 8,951,206 B2 | 2/2015 | Benasisch et al. | |
| 2004/0037236 A1 | 2/2004 | Massey et al. | |
| 2004/0049124 A1 | 3/2004 | Kullok | |
| 2005/0273017 A1 | 12/2005 | Gordon | |
| 2005/0283053 A1 | 12/2005 | deCharms | |
| 2006/0073452 A1 | 4/2006 | Goldman | |
| 2006/0252014 A1 | 11/2006 | Simon et al. | |
| 2006/0292531 A1 | 12/2006 | Gibson | |
| 2007/0009864 A1 | 1/2007 | Rikimaru et al. | |
| 2007/0031798 A1 | 2/2007 | Gottfried | |
| 2007/0134635 A1 | 6/2007 | Hardy | |
| 2007/0141541 A1 | 6/2007 | Chan et al. | |
| 2007/0166675 A1 | 7/2007 | Atkins et al. | |
| 2007/0191727 A1 | 8/2007 | Fadem | |
| 2007/0218440 A1 | 9/2007 | Delahunt et al. | |
| 2007/0293735 A1 | 12/2007 | Chan et al. | |
| 2007/0299319 A1 | 12/2007 | Chan et al. | |
| 2008/0003558 A1 | 1/2008 | Chan et al. | |
| 2009/0005648 A1 | 1/2009 | Teicher et al. | |
| 2009/0306534 A1 | 12/2009 | Pizzagalli | |
| 2009/0312817 A1 | 12/2009 | Hogle et al. | |
| 2009/0319380 A1 | 12/2009 | Jacoby et al. | |
| 2010/0041001 A1 | 2/2010 | Delahunt et al. | |
| 2010/0094162 A1 | 4/2010 | Benasich et al. | |
| 2010/0249532 A1 | 9/2010 | Maddess | |
| 2010/0292545 A1 * | 11/2010 | Berka | A61B 5/168 600/301 |
| 2011/0066071 A1 * | 3/2011 | Duffy | A61B 5/165 600/558 |
| 2012/0271194 A1 * | 10/2012 | MacLullich | A61B 5/742 600/558 |
| 2013/0203027 A1 | 8/2013 | de Villers-Sidani | |
| 2013/0216985 A1 | 8/2013 | de Villers-Sidani | |
| 2014/0148728 A1 | 5/2014 | Eizenman | |
| 2014/0370479 A1 | 12/2014 | Gazzaley | |
| 2016/0117940 A1 | 4/2016 | Gomory | |
| 2016/0267804 A1 | 9/2016 | Pemba | |

FOREIGN PATENT DOCUMENTS

| | | |
|---|---|---|
| JP | 2009237104 | 10/2009 |
| WO | WO 2007070876 | 6/2007 |
| WO | 2008013907 | 1/2008 |
| WO | 2009114795 | 9/2009 |

OTHER PUBLICATIONS

Anguera et al. (2010) "Age-Related Changes in Distraction & Multitasking during a Driving Video Game" Department of Neurology and Physiology, W.M. Keck Center for Integrative Neurosciences, University of California San Francisco, San Francisco, California. Nov. 3, 2010. Abstract.

Berry et al. (2009) "Practice-Related Improvement in Working Memory is Modulated by Changes in Processing External Interference" J Neurophysiol 102:1779-1789.

Bherer et al. (2008) "Transfer effects in task-set cost and dual-task cost after dual-task training in older and younger adults: further evidence for cognitive plasticity in attentional control in late adulthood" Exp Aging Res 34(3):188-219.

Blake & Merzenich (2002) "Changes of AI receptive fields with sound density" J Neurophysiol 88(6):3409-3420.

Blake et al. (2002) "Sensory representation abnormalities that parallel focal hand dystonia in a primate model" Somatosens Mot Res 19(4):347-357.

Carry the One Radio Interview with Adam Gazzaley Jan. 15, 2010. Transcript. http://www.carrytheoneradio.com/2010/01/20/adam-gazzaley/.

Chao & Knight (1997) "Prefrontal deficits in attention and inhibitory control with aging" Cereb Cortex 7:63-69.

Clapp & Gazzaley (2012) "Distinct mechanisms for the impact of distraction and interruption on working memory in aging" Neurobiol Aging 33(1):134-148. doi: 10.1016/j.neurobiolaging.2010.01.012. Epub Feb. 9, 2010.

Clapp et al. (2009) "Mechanisms of working memory disruption by external interference" Cereb Cortex 20:859-872.

Czigler et al. (1992) "Age and Inter-Stimulus Interval Effects on Event-Related Potentials to Frequent and Infrequent Auditory Stimuli" Biol Psychol 33(2-3):195-206.

De Villers-Sidani et al. (2010) "Recovery of Functional and Structural Age-Related Changes in the Rat Primary Auditory Cortex with Operant Training" Proc Natl Acad Sci USA 107(31):13900-13905.

Decharms et al. (1998) "Optimizing sound features for cortical neurons" Science 280(5368):1439-1443.

Draganova et al. (2009) "Modulation of Auditory Evoked Responses to Spectral and Temporal Changes by Behavioral Discrimination Training" BMC Neurosci 143. doi: 10.1186/1471-2202-10-143.

Duncan-Johnson & Donchin (1977) "On Quantifying Surprise: The Variation of Event-Related Potentials with Subjective Probability" Psychophysiology 14(5):456-467.

Gazzaley et al. (2005) "Top-down suppression deficit underlies working memory impairment in normal aging" Nat Neurosci 8(10):1298-1300.

Greenberg & Waldman (1993) "Developmental normative data on the test of variables of attention (T.O.V.A.)" J Child Psychol Psychiatry 34(6):1019-1030.

(56) References Cited

OTHER PUBLICATIONS

Hasher et al. (1991) "Age and inhibition" J Exp Psychol Learn Mem Cogn 17(1):163-169.
Herrmann & Knight (2001) "Mechanisms of Human Attention: Event-Related Potentials and Oscillations" Neurosci Biobehav Rev 25(6):465-476.
Jeon & Polich (2003) "Meta-Analysis of P300 and Schizophrenia: Patients, Paradigms, and Practical Implications" Psychophysiology 40(5):684-701.
Kelland & Lewis (1996) "The Digit Vigilance Test: reliability, validity, and sensitivity to diazepam" Arch Clin Neuropsychol 11(4):339-344.
Kilgard & Merzenich (1998) "Cortical map reorganization enabled by nucleus basalis activity" Science 279(5357):1714-1718.
McIlroy "Does Play Really Keep Dementia at Bay?" Globe and Mail Sep. 22, 2010.
Ophir et al. (2009) "Cognitive control in media multitaskers" Proc Natl Acad Sci USA 106(37):15583-15587.
Rasmusson et al. (1995) "Stability of performance on the Hopkins Verbal Learning Test" Arch Clin Neuropsychol 10(1):21-26.
Robertson & Irvine (1989) "Plasticity of frequency organization in auditory cortex of guinea pigs with partial unilateral deafness" J Comp Neurol 282(3):456-471.
Robertson et al. (1997) "'Oops!': performance correlates of everyday attentional failures in traumatic brain injured and normal subjects" Neuropsychologia 35(6):747-758.
Royan et al. (2004) "The Adjusting-Paced Serial Addition Test (Adjusting-PSAT): thresholds for speed of information processing as a function of stimulus modality and problem complexity" Arch Clin Neuropsychol 19(1):131-143.
Rutkowski et al. (2005) "Encoding of learned importance of sound by magnitude of representational area in primary auditory cortex" Proc Natl Acad Sci USA 102(38):13664-13669.
Siu et al. (2008) "Does inability to allocate attention contribute to balance constraints during gait in older adults?" J Gerontol A Biol Sci Med Sci 63(12):1364-1369.
Smith et al. (2009) "A cognitive training program based on principles of brain plasticity: results from the Improvement in Memory with Plasticity-based Adaptive Cognitive Training (IMPACT) study" J Am Geriatric Soc 57(4):594-603.
Stuss et al. (1987) "Comparison of three tests of attention and rapid information processing across six age groups" Clinical Neuropsychologist 1(2):139-152.
Ulanovsky et al. (2003) "Processing of low-probability sounds by cortical neurons" Nat Neurosci 6(4):391-398.
Van Rossum (2001) "A novel spike distance" Neural Comput 13(4):751-763.
Wilson (2003) "Development of a speech-in-multitalker-babble paradigm to assess word-recognition performance" J Am Acad Audiol 14(9):453-470.
Zhang et al. (2001) "Persistent and specific influences of early acoustic environments on primary auditory cortex" Nat Neurosci 4(11):1123-1130.
Polley et al. (2006) "Perceptual learning directs auditory cortical map reorganization through top-down influences" J Neurosci 26(18):4970-4982.
Adolfsdottir, S., et al., (2008) "The attention network test: a characteristic pattern of deficits in children with ADHD", Behavioral and Brain Functions, 4(9).
Dahlin, E., et al., (2008) "Transfer of learning after updating training mediated by the striatum", Science, 320(5882): 1510-1512.
Eriksen, B. A., & Eriksen, C. W., (1974) "Effects of noise letters upon the identification of a target letter in a nonsearch task", Perception and Psychophysics, 16:143-149.
Fan J, et al., (2002) "Testing the efficiency and independence of attentional networks", J Cogn Neurosci., 14(3):340-7.
Jaeggi SM, et al., (2008) "Improving fluid intelligence with training on working.memory", Proc Natl Acad Sci USA, 105:6829-6833.
Kelly, T.A. & Yantis, S., (2009) "Learning to attend: Effects of practice on information selection", Journal of Vision, 9(7): 1-18.
Klingberg, T., (2010) "Training and plasticity of working memory", Trends in Cognitive Sciences, 14:317-324.
Klingberg, T., et al., (2005) "Computerized training of working memory in children with ADHD—a randomized, controlled trial", Journal of the American Academy of Child and Adolescent Psychiatry, 44(2):177-186.
Klingberg T, et al., (2002) "Training of Working Memory in Children with ADHD", Journal of Clinical and Experimental Neuropsychology, 24(6):781-791.
Lustig, C., et al., (2009) "Aging, training, and the brain: a review and future directions, Neuropsychological Review, 19: 504-522.
Machado, L., et al., (2009) "Distractibility with advancing age and Parkinson's disease", Neuropsychologia, 47(7):1756-64.
Morrison, A.B., et al., (2011) "Does working memory training work? The promise and challenges of enhancing cognition by training working memory", Psychonomic Bulletin Review, 18:46-60.
Olesen P, et al., (2004) "Increased prefrontal and parietal brain activity after training of working memory", Nature Neuroscience, 7(1):75-79.
Olson, I. R., & Jiang, Y., (2004) "Visual short-term memory is not improved by training", Memory & cognition, 32(8): 1326-1332.
Owen AM, et al., (2010) "Putting brain training to the test", Nature, 465:775-778.
Persson, J. & Reuter-Lorenz, P.A., (2008) "Gaining control: training executive function and far transfer of the ability to resolve interference", Psychological Science, 19(9):881-8.
Shipstead, Z., et al., (2010) "Does working memory training generalize?", Psychologica Belgica, 50:245-276.
Third Party Observations, EP11840579.4, (2017), 29 pages.
Jaeggi, Susanne M., et al., (2008) "Improving fluid intelligence with training on working memory", PNAS, 105(19):6829-6833.
Wesley C. Clapp, Michael T. Rubens and Adam Gazzaley "Mechanisms of Working Memory Disruption by External Interference", Jul. 31, 2009, Advance Access Publication, University of California, CA 94158.
Endsley et al. "Disruptions, interruptions and information attack: Impact on situtation awareness and decision making" Clara, CA: SA Technologies, Inc; 2001.
Shiffrin et al. "Controlled and Automatic Human Information Processing:" vol. 84, No. 2, Mar. 1977.

\* cited by examiner

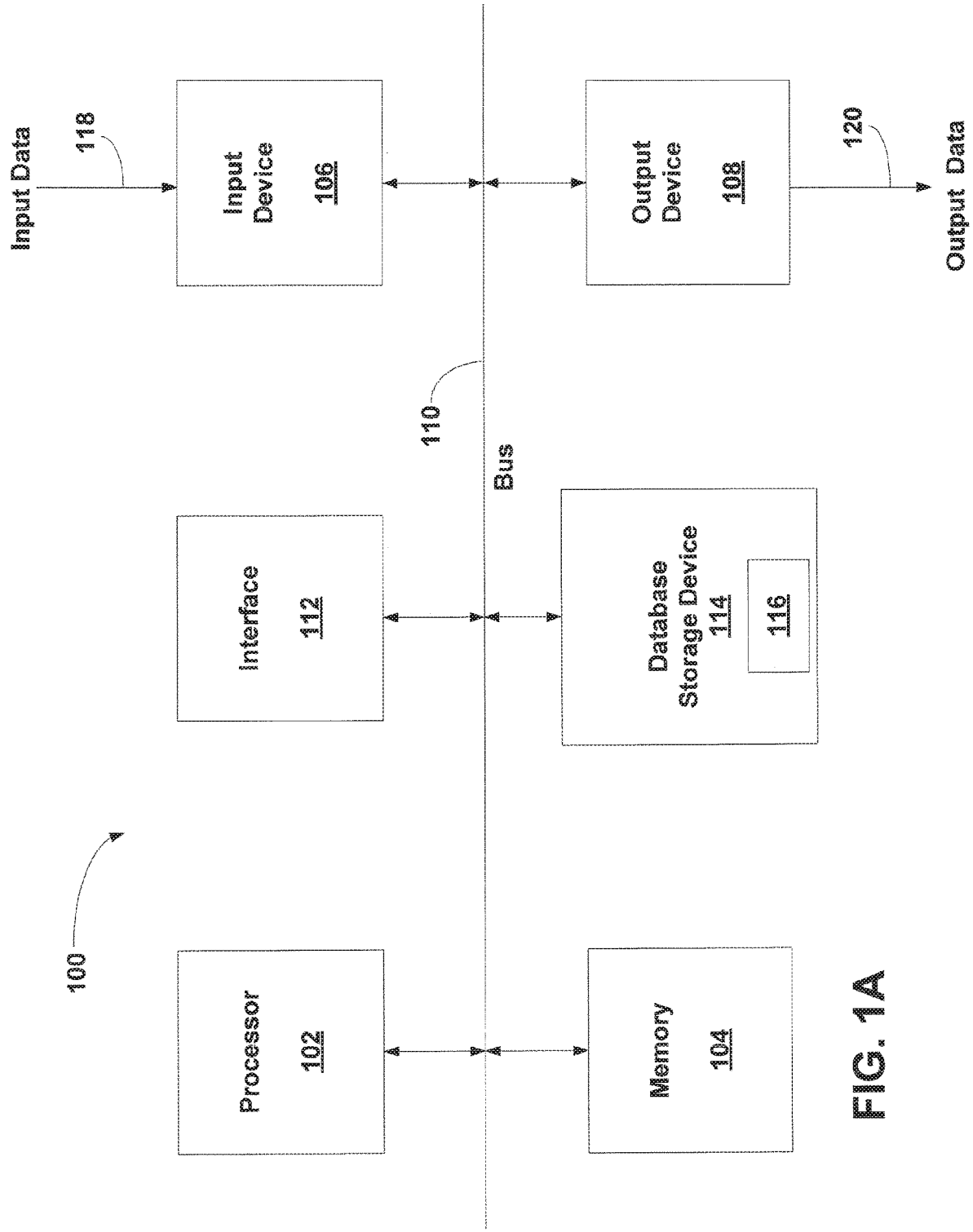

A  Single Task Performance

B  Dual Task Performance

C  Dual-Task Cost

D1 = Dual-Day 1
D2 = Dual-Day 2
S1 = Single-Day 1
S2 = Single-Day 2
C1 = Control-Day 1
C2 = Control-Day 2

ΔD = Dual Difference
ΔS = Single Difference
ΔC = Control Difference

A

B

C

ENHANCING COGNITION IN THE PRESENCE OF DISTRACTION AND/OR INTERRUPTION

CROSS-REFERENCE TO RELATED APPLICATIONS

This applications claims priority benefit of U.S. provisional application Ser. No. 61/412,738, filed Nov. 11, 2010, and Canadian patent application no. 2720892, filed Nov. 12, 2010, each of which are incorporated by reference in its entirety.

INTRODUCTION

Cognitive decline is a near-universal aspect of normal aging. Some deficits are related to processing of auditory and visual data, for example, and the command of motor functions while in an environment with challenging (noisy, time-limited, attentionally-demanding) conditions.

One deficit that distinguishes the young from the old brain is the ability to maintain cognitive performance in the presence of interrupting and distracting stimuli. Other deficits can involve the ability to multi-task and concentrate on performing a task in the presence of distractions.

Accordingly, methods and tools for enhancing cognition are needed. The present disclosure provides methods and tools for improving the cognitive ability in aging individuals, individuals suffering from cognitive impairment, or healthy individuals wishing to enhance their cognitive abilities.

SUMMARY

An aspect of the present disclosure relates to methods and tools for enhancing cognition in an individual, e.g., by improving the individual's ability to deal with interference in cognitive function. The training methods can involve presenting to an individual a task to be performed, presenting to the individual an interference, and receiving inputs from the individual. Where the interference is a distraction, the individual is to ignore the interference. Where the interference is an interruptor, the individual is instructed to respond to the interruptor as a secondary task and is said to be multi-tasking. Inputs can also be received from the individual pertaining to this secondary task. The methods encompass iterations of various presentating steps and receiving of the input. The methods can further include conducting an analysis and/or generating feedback to the individual. The analysis can include a comparison of the performances with or without each type of interference, and, in some embodiments, the difficulty of the task may be modulated as a function of this comparison. Another aspect of the present invention provides presenting tasks with increasing levels of interference. Diagnostic methods are also provided herein and are used to assess cognitive ability of an individual independent of or in combination of the training methods disclosed herein. The diagnostic methods can include the step of measuring the disparity between performance on a baseline task and that baseline task when presented along with interference, analyzing that disparity, and providing feedback of that information to either drive a diagnostic decision or modulate the training protocol.

In one embodiment, the present disclosure provides computer-implemented methods for enhancing cognitive skills in an individual, wherein the method is implemented using a computer device having a display component and an input device comprising presenting at least a visual task to the individual using the display component requiring a response from the individual via the input device; presenting at least a first interference with the first task, wherein the first interference diverts the individual's attention from the visual task; obtaining in the computer device the individual's response to the at least a visual task; and analyzing in the computer device the difference in the individual's performance when performing the at least a visual task without interference and with interference to determine an individual's cognitive skills.

In related examples of embodiments, the computer-implemented method can further including the steps of presenting at least a visual task, presenting at least a first interference, and obtaining in the computer device the individual's responses in an iterative manner.

In further examples, the analyzing step can include determining whether the individual responded correctly to each visual task. In further examples, the computer-implemented method can further include the step of modifying the difficulty of the at least a visual task based on the analyzing step. In related examples, the step of modifying the difficulty of the at least a visual task can include one or more of modifying a visual emphasis of at least one foreground object and/or background object to modify the at least a visual task. In related examples, modifying the visual emphasis can include adjusting the degree of visual emphasis according to one or more visual emphasis techniques.

In related examples of embodiments, each of the one or more visual emphasis techniques specifies a corresponding attribute, wherein the adjusting the degree of visual emphasis includes increasing the visual emphasis of the scene, and wherein increasing the visual emphasis of the scene includes increasing the attribute for the at least one foreground object according to a first visual emphasis technique. In related examples, each of the one or more visual emphasis techniques specifies a corresponding attribute, wherein the adjusting the degree of visual emphasis includes increasing the visual emphasis of the scene, and wherein the increasing the visual emphasis of the scene includes decreasing the attribute for the background according to a first visual emphasis technique. In related examples, the one or more visual emphasis techniques specifies a corresponding attribute, wherein the adjusting the degree of visual emphasis includes increasing the visual emphasis of the scene, and wherein the increasing the visual emphasis of the scene includes: increasing the attribute for the at least one foreground object according to a first visual emphasis technique; and decreasing the attribute for the background according to the first visual emphasis technique. In further examples, each of the one or more visual emphasis techniques specifics a corresponding attribute, wherein the adjusting the degree of visual emphasis includes increasing the visual emphasis of the scene, and wherein the increasing the visual emphasis of the scene includes: increasing the attribute for the at least one foreground object according to a first visual emphasis technique; and decreasing the attribute for the background according to a second visual emphasis technique. In further examples, each of the one or more visual emphasis techniques specifies a corresponding attribute, wherein the adjusting the degree of visual emphasis includes decreasing the visual emphasis of the scene, and wherein the decreasing the visual emphasis of the scene includes decreasing the attribute for the at least one foreground object according to a first visual emphasis technique. In further examples, each of the one or more visual emphasis techniques specifies a corresponding attribute, wherein the adjusting the degree of visual emphasis includes decreasing the visual emphasis of the scene, and wherein the decreasing the visual emphasis of the scene includes decreasing the attribute for the background according to a first visual emphasis technique. In further examples, each of the one or more visual emphasis techniques specifies a corresponding attribute, wherein the adjusting the degree of visual emphasis includes decreasing the visual emphasis of the scene, and wherein the decreasing the visual emphasis of the scene includes decreasing the attribute for the at least one foreground object according to a first visual emphasis technique; and increasing the attribute for the background according to the first visual emphasis technique. In further examples, each of the one or more visual emphasis techniques specifies a corresponding attribute, wherein the adjusting the degree of visual emphasis includes decreasing the visual emphasis of the scene, and wherein the decreasing the visual emphasis of the scene includes decreasing the attribute for the at least one foreground object according to a first visual emphasis technique; and increasing the attribute for the background according to a second visual emphasis technique.

In some embodiments, the visual task is selected from the group consisting of and relating to individual's attention, memory, motor, reaction, executive function, decision-making, problem-solving, language processing and comprehension skills.

In some embodiments, the presenting at least a first interference includes presenting a plurality of interferences.

In some embodiments, the at least a first interference is presented during only a portion of the at least a visual task. In some embodiments, the at least a first interference is presented during the entire portion of the at least a visual task.

In some embodiments, the at least a first interference is from a same cognitive domain as the at least a visual task.

In some embodiments, the at least a first interference is from a different cognitive domain as the at least a visual task.

In some embodiments, the at least a first interference is a distraction requiring no user response. In some embodiments, the at least a first interference is an interruption requiring a user response.

In some embodiments, the computer device is selected from the group consisting of a desktop computer, a laptop computer, a computer tablet device, a smart phone device and a video game device. In some embodiments, the computer input device is selected from the group consisting of a mouse component a stylus computer, a keyboard component and a touch-screen display.

In one embodiment, the present disclosure provides computer-implemented methods for diagnosing cognitive function of an individual, wherein the method is implemented using a computer device having an input component, comprising presenting at least a first task to the individual requiring a response from the individual via the input device; presenting at least a first interference with the first task; obtaining in the computer input component the individual's responses to the at least a first task; analyzing in the computer device the difference in the individual's performance when performing the at least the first task without interference and with interference to determine an individual's cognitive function; and providing an output from the computer device indicative of the individual's determined cognitive function.

In some embodiments, the analyzing step includes diagnosing a disease or illness associated with the individual.

In some embodiments, the first task is a visual task. In some embodiments, the first task is selected from the group consisting of and relating to individual's attention, memory, motor, reaction, executive function, decision-making, problem-solving, language processing and comprehension skills.

In some embodiments, the presenting at least a first interference includes presenting a plurality of interferences.

In some embodiments, the at least a first interference is presented during only a portion of the at least a first task. In some embodiments, the at least a first interference is presented during the entire portion of the at least a first task.

In some embodiments, the at least a first interference is from a same cognitive domain as the at least a first task. In some embodiments, the at least a first interference is from a different cognitive domain as the at least a first task.

In some embodiments, the at least a first interference is a distraction requiring no user response. In some embodiments, the at least a first interference is an interruption requiring a user response.

In some embodiments, the computer device is selected from the group consisting of a desktop computer, a laptop computer, a computer tablet device, a smart phone device and a video game device. In some embodiments, the computer input device is selected from the group consisting of a mouse component, a stylus computer, a keyboard component and a touch-screen display.

In one embodiment, the present disclosure provides computer-implemented methods for enhancing cognition of an individual by training the individual to process interference in conjunction with a task, wherein the method is implemented using a computer device having an input device comprising presenting at least a first task having a difficulty level to the individual requiring a response from the individual via the input device; presenting at least a first interference with the first task; obtaining in the computer input device the individual's responses to the at least a first task; analyzing in the computer device the individual's performance regarding responses to each presented first task; presenting the at least a first task, at least a first interference and obtaining in the computer device the individual's responses in an iterative manner, adjusting the difficulty level of the at least a first task based upon the individual's performance determined in the analyzing step; and providing an output from the computer device indicative of the individual's cognitive function.

In some embodiments of such methods, the analyzing step comprises comparing the individual's performance to a determined threshold performance level of the individual relative to each performed task and associated interference.

In some embodiments, the step of adjusting the difficulty level is dependent upon the individual's performance when performing a task without interference and when performing a task with interference.

In some embodiments, when an individual's determined performance is below a prescribed threshold level, the difficulty of the task is adjusted via presentation of a new interference. In some embodiments, the new interference is in addition to an existing interference.

In some embodiments, the analyzing step includes diagnosing a disease or illness associated with the individual.

In some embodiments, the first task is a visual task. In some embodiments, the first task is selected from the group consisting of and relating to individual's attention, memory, motor, reaction, executive function, decision-making, problem-solving, language processing and comprehension skills.

In some embodiments, the presenting at least a first interference includes presenting a plurality of interferences.

In some embodiments, the at least a first interference is presented during only a portion of the at least a first task.

In some embodiments, the at least a first interference is presented during the entire portion of the at least a first task, of such methods the at least a first interference is from a same cognitive domain as the at least a first task.

In some embodiments, the at least a first interference is from a different cognitive domain as the at least a first task.

In some embodiments, the at least a first interference is a distraction requiring no user response. In some embodiments, the at least a first interference is an interruption requiring a user response. In some embodiments, the computer device is selected from the group consisting of a desktop computer, a laptop computer, a computer tablet device, a smart phone device and a video game device. In some embodiments, the computer input device is selected from the group consisting of a mouse component, a stylus computer, a keyboard component and a touch-screen display.

In one embodiment, the present disclosures provides a computer-readable memory medium that stores program instructions for enhancing cognition in an individual, utilizing a computing device to present tasks for training, and to receive responses from the individual, wherein the program instructions are executable by a processor to perform: presenting at least a visual task to the individual using the display component requiring a responses from the individual via the input device; presenting at least a first interference within the first task, wherein the first interference diverts the individuals attention from the visual task; obtaining in the computer device the individual's responses to the at least a visual task; and analyzing in the computer device the difference in the individual's performance when performing the at least a visual task without interference and with interference to determine the individual's cognitive skills.

In one embodiment, the present disclosure provides a computer-readable memory medium that stores program instructions for enhancing cognition in an individual, utilizing a computing device to present tasks for training, and to receive responses from the individual, wherein the program instructions are executable by a processor to perform: presenting at least a first task to the individual requiring a response from the individual via the input device; presenting at least a first interference with the first task; obtaining in the computer input component the individual's responses to the at least a first task; analyzing in the computer device the difference in the individual's performance when performing the at least a first task without interference and with interference to determine an individual's cognitive function; and providing an output from the computer device indicative of the individual's determined cognitive function.

In some embodiments, the present disclosure provides a computer-readable memory medium that stores program instructions for enhancing cognition in an individual, utilizing a computing device to present tasks for training, and to receive responses from the individual, wherein the program instructions are executable by a processor to perform: presenting at least a first task having a difficulty level to the individual requiring a response from the individual via the input device; presenting at least a first interference with the first task; obtaining in the computer input component the individual's responses to the at least a first task; analyzing in the computer device the individual's performance regarding responses to each presented first task; presenting the at least a first task, at least a first interference and obtaining in the computer device the individual's responses in an iterative manner; adjusting the difficulty level of the at least a first task based upon the individual's performance determined in the analyzing step; and providing an output from the computer device indicative of the individual's cognitive function.

In one embodiment, the present disclosure provides methods of training to enhance cognition in an individual comprising presenting a task to the individual, presenting an interference to the individual, wherein the interference is either a distractor or an interruptor; receiving a first input from the individual that has been instructed to respond to the task; if the interference is an interruptor, receiving a second input from the individual that has been instructed to respond to the interruptor; and repeating the previous presenting and the receiving steps continuously in a first trial; and initiating a second trial of the presenting and receiving steps; i) wherein if the number of correct inputs in the first trial reaches a threshold, the second trial has a higher difficulty level than the first trial, and ii) wherein if the number of correct inputs in the first trial is below the threshold, the second trial has lower difficulty level than said first trial; and generating an output comprising: i) an analysis of the performance of the individual in the presence of interference; and ii) an analysis of the performance of the individual in the absence of interference, wherein the method enhances cognition in the individual.

In some embodiments, the interference comprises only distractor and does not comprise an interruptor as interference in any trial. In some embodiments, the interference comprises only interruptor and does not comprise a distractor as interference in any trial.

In some embodiments, analysis of the performance in the presence of interference comprises: an analysis of the performance in the presence of a distractor; and an analysis of the performance in the presence of an interruptor.

In some embodiment, the method comprises an assessment prior to the first presenting step, wherein such assessment comprises presenting a task to the individual in the absence of interference.

In some embodiments, the first trial is at a difficulty level, which corresponds to about 80% correct responses to the task in the absence of interference.

In some embodiments, the interference is an interruptor.

In some embodiments, the steps of presenting a task and presenting an interference occurs concurrently.

In some embodiments, the step of presenting an interference occurs in the same frequency throughout a trial.

In some embodiments, the method includes generating a feedback as an output that indicates real-time performance of the individual during a trial.

In some embodiments, the task and the interruptor are visual-motor tasks. In some embodiments, the task is a visual-motor task and the interruptor is an auditory task. In some embodiments, the task and the interrupter are auditory tasks. In some embodiments, the task is a target discrimination task or a tracking task.

In some embodiments, the interruptor is a target discrimination task or a tracking task. In some embodiments, the tracking task comprises presenting a moving vehicle on a winding path and the input of the individual comprises navigating the vehicle on the path. In some embodiments, a difficulty level of the moving vehicle is based on speed of the vehicle.

In some embodiments, the target discrimination task comprises presenting a plurality of visual stimuli sequentially and the input of the individual comprises pressing a button when a target stimuli appears on a screen. In some embodiments, the target stimuli is of a specific colored shape.

In one embodiment, the present disclosure provides a computer accessible memory medium comprising program instructions wherein execution of the instructions causes a device to perform a method disclosed herein.

In one embodiment, the present disclosure provides methods of training for enhancing cognition in an individual comprising executing instructions using a computer system to presenting a task to the individual, presenting an interference to the individual, wherein the interference is either a distractor or an interruptor; receiving a first input from the individual that has been instructed to respond to the task; if the interference is an interruptor, receiving a second input from the individual that has been instructed to respond to the interruptor; and repeating the previous presenting and the receiving steps continuously in a first trial; and initiating a second trial of the presenting and receiving steps; i) wherein if the number of correct inputs in the first trial reaches a threshold, the second trial has a higher difficulty level than the first trial, and ii) wherein if the number of correct inputs in the first trial is below the threshold, the second trial has lower difficulty level than the first trial; and generating an output comprising: i) an analysis of the performance of the individual in the presence of interference; and ii) an analysis of the performance of the individual in the absence of interference, wherein the method enhances cognition in the individual.

BRIEF DESCRIPTION OF FIGURES

FIG. 1A is an illustrated embodiment of a computering device used with the present invention;

DETAILED DESCRIPTION OF EXEMPLARY EMBODIMENTS

Figure 1B:
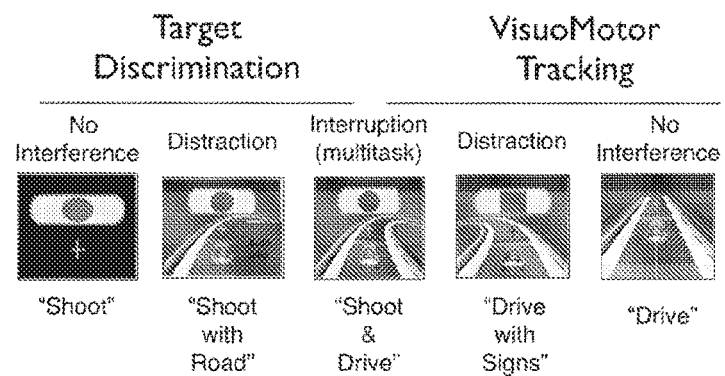
FIG. 1B illustrates pictorial representations of certain categories of tasks and stimuli for an embodiment of the present disclosure in accordance with illustrated embodiments of the present invention.

The present invention is now described more fully with reference to the accompanying drawings, in which an illustrated embodiment of the present invention is shown. The present invention is not limited in any way to the illustrated embodiment as the illustrated embodiment described below is merely exemplary of the invention, which can be embodied in various forms, as appreciated by one skilled in the art. Therefore, it is to be understood that any structural and functional details disclosed herein are not to be interpreted as limiting, but merely as a basis for the claims and as a representative for teaching one skilled in the art to variously employ the present invention. Furthermore, the terms and phrases used herein are not intended to be limiting but rather to provide an understandable description of the invention.

It is to be appreciated the embodiments of this invention as discussed below can be a software algorithm, program or code residing on computer useable medium having control logic for enabling execution on a machine having a computer processor. The machine typically includes memory storage configured to provide output from execution of the computer algorithm or program.

Turning now descriptively to the drawings, in which similar reference characters denote similar elements throughout the several views, FIG. 1A depicts an exemplary general-purpose computing system in which illustrated embodiments of the present invention may be implemented.

A generalized computing embodiment in which the present invention can be realized is depicted in FIG. 1A illustrating a processing system 100 which generally comprises at least one processor 102, or processing unit or plurality of processors, memory 104, at least one input device 106 and at least one output device 108, coupled together via a bus or group of buses 110. In certain embodiments, input device 106 and output device 108 could be the same device. An interface 112 can also be provided for coupling the processing system 100 to one or more peripheral devices, for example interface 112 could be a PCI card or PC card. At least one storage device 114 which houses at least one database 116 can also be provided. The memory 104 can be any form of memory device, for example, volatile or non-volatile memory, solid state storage devices, magnetic devices, etc. The processor 102 could comprise more than one distinct processing device, for example to handle different functions within the processing system 100. Input device 106 receives input data 118 and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data 118 could come from different sources, for example keyboard instructions in conjunction with data received via a network. Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 could be distinct and derived from different output devices, for example a visual display on a monitor in conjunction with data transmitted to a network. A user could view data output, or an interpretation of the data output, on, for example, a monitor or using a printer. The storage device 114 can be any form of data or information storage means, for example, volatile or non-volatile memory, solid state storage devices, magnetic devices, etc.

In use, the processing system 100 is adapted to allow data or information to be stored in and/or retrieved from, via wired or wireless communication means, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 can be provided. It should be appreciated that the processing system 100 may be any form of terminal, server, specialized hardware, or the like.

It is to be appreciated that the processing system 100 may be a part of a networked communications system. Processing system 100 could connect to a network, for example the Internet or a WAN. Input data 118 and output data 120 could be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the processing computing system environment 100 illustrated in FIG. 1A may operate in a networked environment using logical connections to one or more remote computers. The remote computer may be a personal computer, a server, a router, a network PC, a peer device, or other common network node, and typically includes many or all of the elements described above.

It is to be further appreciated that the logical connections depicted in FIG. 1A include a local area network (LAN) and a wide area network (WAN), but may also include other networks such as a personal area network (PAN). Such networking environments are commonplace in offices, enterprise-wide computer networks, intranets, and the Internet. For instance, when used in a LAN networking environment, the computing system environment 100 is connected to the LAN through a network interface or adapter. When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 1A are exemplary and other means of establishing a communications link between multiple computers may be used.

FIG. 1A is intended to provide a brief, general description of an illustrative and/or suitable exemplary environment in which embodiments of the below described present invention may be implemented. FIG. 1A is an example of a suitable environment and is not intended to suggest any limitation as to the structure, scope of use, or functionality of an embodiment of the present invention. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

In the description that follows, certain embodiments may be described with reference to acts and symbolic representations of operations that are performed by one or more computing devices, such as the computing system environment 100 of FIG. 1A. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, personal digital assistants, multiprocessor systems, microprocessor-based systems, set top boxes, programmable consumer electronics, network, minicomputers, server computers, game server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media including memory storage devices.

With the exemplary computing system environment 100 of FIG. 1A being generally shown and discussed above, description will now turn towards illustrated embodiments of the present invention which generally relates to methods for enhancing cognition in an individual. It is to be understood and appreciated the methods involve presenting to an individual a task to be performed, presenting to the individual an interference, and receiving inputs from the individual. Where the interference is a distraction, the individual is to ignore the interference. Where the interference is an interruptor, the individual is instructed to respond to the interruptor as a secondary task and is said to be multi-tasking.

The present invention is based in part on the recognition that interference in cognitive function can be specifically measured and trained, and, further, that the distraction and multi-tasking (interruption) aspects of interference are separable and can be separately trained. The present disclosure thus provides methods and systems that provide for separately evaluating the ability to resist distraction and the ability to multi-task, and that provide for separately training the ability to resist negative effects of distraction and enhancing the ability to multi-task.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

Definitions

When describing the methods and compositions of the present disclosure, the following terms include the following meanings unless otherwise indicated within the present disclosure, but the terms are not to be understood to be limited to their accompanying meaning as rather it is to be understood to encompass any meaning in accordance with the teachings and disclosure of the present invention.

The term "cognition", as used herein, can include, but is not limited to, domains such as perception, attention, memory, motor function, problem solving, language processing, decision making and intelligence.

"Targets," as used herein, may be both concrete (e.g., a visual focal point such as a person or sign, or an auditory focal point such as a tone or conversation) as well as abstract (e.g., a concept in one's thought process such as an idea or memory or representation of an event).

The term "memory" may additionally refer to the ability of an individual to learn and retain information either in the long term or the short term.

The term "perception" may additionally refer the ability of an individual to receive and process stimuli.

The term "inter-stimulus-interval (ISI)", refers to a specified amount of time between ceasing presentation of a stimulus and presenting a next stimulus in a sequence. For example, a secondary stimulus in the methods of the present disclosure can be presented repeatedly in a sequence with a gap of two seconds.

The term "target stimulus", as used herein, refers to a stimulus that is arbitrarily chosen by the method or device to be the focus point among a group of different stimuli presented to an individual. An individual is instructed as to the one or more properties that distinguish the target stimulus from the non-target stimulus. The target stimulus differs in at least one property from a non-target stimulus.

As used herein, the term "non-target stimulus" refers to a stimulus that is not the focus point due to a difference in at least one or more different properties. A non-target stimulus may differ from a target stimulus but is not necessarily the same as another non-target stimulus.

The term "task" refers to a goal and/or objective to be accomplished by an individual who provides a response to a particular stimulus. For example, the individual would have been instructed to perform a specific goal. The "task" can serve as the baseline cognitive function that is being performed and measured, and to which interference is added. Thus, a "task" often refers to the main goal that an individual is instructed to perform in either the presence or absence of interference.

The term "interference" with reference to a specific function, as used herein, refers to any stimulus presented to an individual that has the potential interfere with the performance of a primary task. Interference may be present from one or more of a variety of modalities, including visual, auditory, mental (internal), or other modes. Interference can be generally classified as a distraction or an interruptor that is presented to an individual when the individual is engaged in performing a task. An interference is a "distractor" or "distraction" if the individual is instructed to ignore the interference. Where the interference is a stimulus to which the individual is instructed to respond, the interference is referred to herein as an "interruptor" or an "interruption". Performing a task in the presence of an interruptor causes the individual to carry out both a primary task and a secondary task. As such, the individual is said to be multi-tasking in the presence of an interruptor.

The term "interference cost" of a given function, as used herein, refers to the difference in performance between the function performed in a baseline environment and the function performed in an environment with one or more interference.

Methods

The methods of the present disclosure, in accordance with certain illustrated embodiments of the invention, enhance cognition by training an individual to perform a task in the presence of interference, and assess an individual with respect to the individual's susceptibility to interference in cognitive function. The determination of an Interference Cost, or the difference between an individual's performance on a task in isolation versus a task with one or more interference applied, is a core metric used to assess or diagnose the individual, and to determine difficulty and progression of the training in some embodiments. The interference can be presented to the individual either as a distractor or an interruptor. As noted above, a distractor requires no response from the individual, whereas an interruptor does require a response.

The stimuli pertaining to a task and those pertaining to the interference can be presented concurrently or sequentially to the individual. In most instances, the task is continuously engaging the individual and hence, the interference occurs concurrently with the task. However, the interference can be applied at the end of the task or at interim times during the task (e.g., jittered or varied in time to the onset of task engagement) so as to modulate the degree of interference. The interference can be presented to the individual either as a distractor or an interruptor. As noted above, a distractor requires no response from the individual, whereas an interruptor does.

Figure 10:
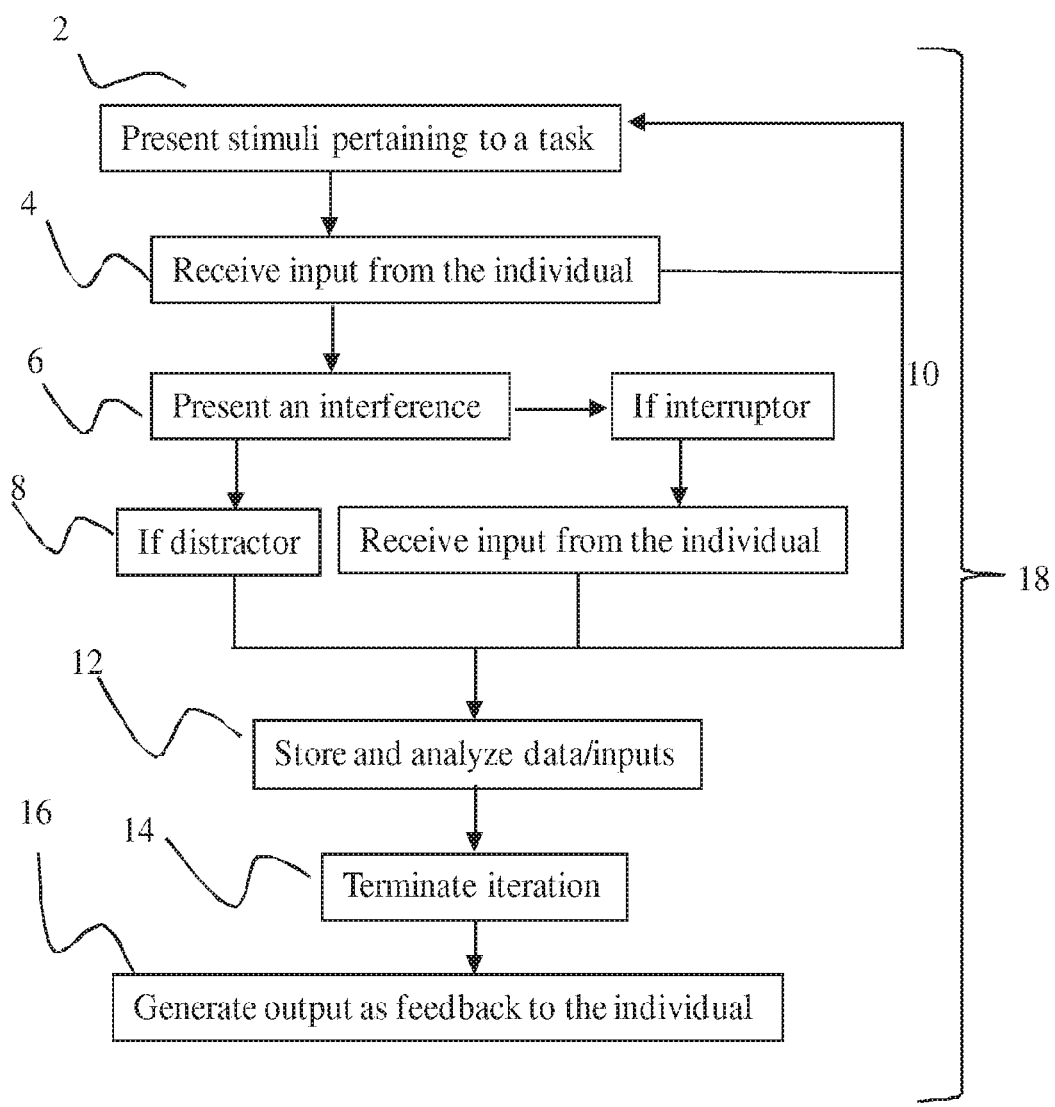
FIG. 10 is a flow diagram illustrating steps of a trial and training session in accordance with illustrated embodiments of the present invention.

Referring to FIG. 10, a method in accordance with an illustrated embodiment of the present invention involves the steps of presenting stimuli pertaining to a task (step 2), receiving a first input from the individual (step 4), presenting an interference (step 6), optionally receiving a second input (step 8), if the interference is an interruptor, and repeating (step 10) the aforementioned presenting and receiving steps. The method can further encompass storing and analyzing the inputs to evaluate and compare the performances of the individual in the presence or absence of an interference and in the presence of a distraction versus an interruption.

It is to be understood the individual being trained by the subject method can be instructed with respect to the presented stimulus in the following ways. In response to stimuli pertaining to a task, the individual is instructed to perform a primary task. As for stimulus that is an interference, if the interference is an interruptor, the individual is instructed to respond to the interruptor by performing a secondary task. As such, where the interference is an interruptor, a secondary input is received from said individual in step 8. If the interference is a distractor, the individual is instructed to not attend to the distractor and no input is expected to be received from the individual. These presenting and receiving steps are then reiterated (step 10) in trial 18 that lasts for a specific duration of time. Where there are two or more trials in a period of time, a group of two or more trials is referred to herein as a training session.

It is understood that steps in FIG. 10 can be initiated before the completion of previous steps. For example, in some embodiments, steps 2 and 4 in FIG. 1A are being performed continuously in time through step 8.

In one illustrative embodiment of the methods of the present invention, the presentation of an interference 6 and input from the individual 8 are conducted in a time interval that is smaller than and contained within the time frame that the task stimulus 2 and receipt of input for the task 4 is completed. Examples include cognitive tasks such as memory performance, where an the individual will need to hold in mind a stimulus, is presented an interference for a short time after which the interference is removed, and then provides an input on the primary memory task. In these cases, the processing of interference in steps 6 and 8 can be conducted either in the middle of the time frame of the task, or closer to the beginning or end of the task. The interference may be presented and/or a require an input from the individual on the order of between 1% and 10% of the time of the original task, or between 5% and 20% of the time of the task, or between 10% and 50% of the time of the task, or between 25% and 75% of the time of the task.

In another illustrated embodiment of the methods of the present invention, the performance of the interference (steps 6 and 8) is conducted continuously and on substantially the same timescale as the performance of the task (steps 2 and 4). In these cases, the interference is presented to the individual at essentially at the same time as the presentation of the task stimuli, and the receiving input from the individual with regard to both the task and the interference are completed at the same time. In these cases, the stimuli and receipt of input of task and interference may be perfectly synchronous (at the same moment) throughout the trial, or may be staggered (such as task, interference, task, interference, etc.) throughout the trial, or may be randomized throughout the trial. An example includes a primary task of responding to targets that are presented with a given frequency, with an interference of continuously navigating on a path.

One or more task and one or more interference may be performed during a trial. The tasks and interferences can be from the same cognitive domain (including but not limited to perception, attention, memory, and motor function) or different cognitive domains during the task, and can stay consistent throughout the task or can vary during completion of the task. Likewise, the tasks and interferences can be from the same or different cognitive domains and can stay consistent or vary during a training session.

The method further involves storing and analyzing the received inputs in step 12 and generating an output in step 16 in system 100. Analysis and output can take many forms and are discussed in more detail below. Briefly, the analysis, which can be via system 100 evaluates the performance of the individual based on the accuracy of the output in the context of different types of interference (e.g., distraction v. interruption) and/or in the absence of interference. In one exemplary embodiment of the methods of the invention, presented in FIG. 11, the analysis is an assessment of the susceptibility to interference, or interference cost. A task is presented (step 20) and input received (step 22), with the input stored for later comparison (step 24). Additionally, the same task but with interference added is presented (step 26) and input received (step 28) and stored (step 30). The inputs from the baseline task and task with interference are then compared and analyzed 32. In a another further embodiment, they are compared by a simple difference between performance of the baseline task versus the task with interference. It is to be understood alternative statistical analysis to compare the inputs and validate the significance of the inputs with data processing techniques known in the art are also suitable. The data obtained from the comparison on the inputs from baseline task versus task with interference may then be generated as output to either the individual to enable assessment or diagnosis (discussed further below) and/or to the entity controlling the trial or training session to guide decisions with respect to the ensuing trial and/or training session via system 100 (discussed below).

It is to be understood that the order of operations can be switched, such that an assessment of the task with interference is conducted before the assessment of the baseline task, and the results will be the same. In some cases it may be desirable to have either the isolated task or the task with interference come first. As above, the task and/or interference can be presented as one or more of a variety of types of cognitive functions and modalities.

The analysis helps to determine the next difficulty and/or next set of task and interference stimuli that the individual will be presented, as discussed below in more detail. In one illustrated embodiment, such an analysis is used to determine the next interference that an individual will be exposed to. In the case that the individual is susceptible to a given interference or has not substantially changed their susceptibility to that interference from a previous analysis (as determined by the individual failing to perform under a maximum value of susceptibility to interference, or interference cost), the next trial presented to the individual can contain substantially the same task(s) and interference(s) as in the previous trial or training session they performed. Alternatively, in the case that the individual is not susceptible to interference, or is less susceptible to interference than they previously were in a previous analysis (as determined by the performing within a pre-defined maximum value of susceptibility to interference, or interference cost), the individual can be presented with a new, more challenging task and interference that will be assessed as to whether it introduces an interference cost. Once the individual is assessed to have a significant interference cost (above a pre-defined value), then the individual will begin a trial and/or training session on that task and interference.

It is to be understood and appreciated this process described above of increasing the interference presented to an individual based on an analysis of their susceptibility to interference, or interference cost, can be a reiterating, cyclical process in which once an individual has been determined to have minimized interference cost for a given task and interference, the individual performs a more challenging task and/or interference until they minimize interference cost in that given condition, at which point they are presented with a still more challenging task and/or interference until they have minimized their interference cost for that condition, and this can repeat nearly indefinitely or to a given termination or end point.

The present methods of the illustrated embodiment of the invention are presented to an individual in two or more trials, with an inter-trial interval in between each trial. The difficulty level in each trial can be dependent on the performance of the individual in the previous trial. If the number of correct inputs in a previous trial reaches a specific threshold, the subsequent trial has a higher difficulty level than the previous trial. However, if the number of correct inputs is below the threshold in the previous trial, the subsequent trial would have a lower difficulty level than the previous trial. Alternatively, the difficulty level can also be designed in a step-wise and/or in a peaks and valley fashion. Below, further details are discussed.

Task and Interference

It it is to be understood and appreciated a task refers to a goal and/or objective to be accomplished by an individual who provides a response to a particular stimulus. Tasks can be selected from any variety of cognitive or behavioral modality, including, but not limited to, fundamental functions such as perception, attention, memory, or motor function, and higher-order processes such as decision-making, intelligence, and the like. An example of a task is one in which the individual pays attention to the stimulus presented, processes the information of the stimulus, and responds as instructed. Certain tasks include detection tasks, target discrimination tasks, tracking tasks, acting on a cue, and other data processing tasks, such as responding to a question. Detection task requires an individual to respond to an occurrence of a stimulus (e.g. a sound or the appearance of an object on a screen). Target discrimination requires an individual to identify a target stimulus from a non-target. A tracking task can involve tracking a path that changes in direction, or pinpointing a moving target. Other examples of a task include carrying on a conversation, typing/writing, physical fitness (e.g. running, walking, biking), reading, shooting, controlling a character on a screen, playing a sport, formulating a strategic decision, keeping an object in memory or reporting on an object contained in memory and the like.

Where the individual is presented only with stimuli that pertain to one task, the individual is said to be performing the task without interference. When the individual performs the same or substantially similar task that has an additional element that has the potential to decrease performance of the first task, that element is called an interference. Like tasks, interference can also be selected from any variety of cognitive or behavioral modality known in the art, including but not limited to, fundamental functions such as perception, attention, memory, or motor function, and higher-order processes such as decision-making, intelligence, and the like.

Where there is interference and the interference is a distractor, the individual performs the task in the presence of the distractor and is instructed not to pay attention to the distractor. For example, the task may be navigating a car on a winding path while colored shapes appear and disappear on the screen above the path intermittently throughout the trial. Since the colored shapes are stimuli that require no response from the individual, the individual is said to be performing the task in the presence of an interference that is a distractor. Conversely, the task may be a target discrimination task, in which the individual is instructed to press a button in response to a green circle that appears on the screen. A car advancing on a path on its own in the background is then a distraction to the target discrimination task.

Where the interference is an interruptor, the individual performs the task in the presence of stimuli that do not pertain to the task, and the individual is instructed to respond to the interruptor. For example, the task may be navigating car on a winding path and, if a green circle appears on the top of the screen, the individual is required to press a button. Since green circles, among other colored shapes, are stimuli that require a specific response from the individual, the individual is said to be performing the task in the presence of an interruptor. Since the individual is actually performing two tasks, one task is referred to as the primary and the other is secondary. The interruptor is considered a stimulus that pertains to the secondary task in the methods of the present disclosure. In the presence of an interruptor, the individual can also be described as multi-tasking. Interruption may be similar or different in nature from the task, and may be in the same domain (e.g. presented visually in front of or next to the task focal point) or in an orthogonal domain (e.g. a signal requiring the individual to engage in a different perceptual domain such as visual vs. auditory) or to perform a secondary motor task unrelated to the primary task (e.g., verbal vs. manual). Below, details of such variety are discussed.

The type of task and the type of stimulus to be presented as interference can be selected from a variety of stimuli and in any combinations as described below. The performance in a specific type of task and/or the response to a specific type of stimulus is an indication of the cognitive ability related to the specific type. For example, a visuomotor tracking task involves visual and motor sensory skills, while auditory stimuli can involve speech and/or auditory skill. In a trial or in a training session with two or more trials, the individual may be presented with the same task but different interferences or alternatively, same interference but different tasks. For example, the methods can present tracking as a primary task and target discrimination as a secondary task or vice versa. In another example, the distractor can be either the appearance and disappearance of colored shapes or a series of motion picture frames of a car driving on a road. Any other permutations that involve different sensory stimuli and motor and speech commands of the individuals can be incorporated.

Trial and Session

In accordance with an illustrative embodiment, the method of the invention can include presenting two or more trials to an individual where each trial contains a series of presenting and receiving steps set forth above and as seen in FIG. 10. Referring to FIG. 10, a trial is the series of steps and iterations represented by reference numeral 18, optionally including an outputting step 16. The length of a trial depends on the number of iterations of presenting and receiving steps and can vary in time. For instance it can last for as long as about 500 milliseconds, about 1 second (s), about 10 s, about 20 s, about 25 s, about 30 s, about 45 s, about 60 s, about 2 minutes, about 3 minutes, about 4 minutes, up to about 5 minutes or more. The length of each trial may be pre-determined or may be flexible and determined by the individual or a dynamic decision by the entity controlling the training session. Where the trial length is flexible, it may be dependent on the length the individual desires. Alternatively, the trial length can be dependent on whether a performance level or a training goal has been reached. The time interval between trials can be referred to herein as "inter-trial" interval. Similarly, inter-trial interval can be pre-determined or dependent on the individual's liking. For example, where an inter-trial interval is within a 24-hour period, the interval can be about a few seconds, about 500 milliseconds, about 1 second, about 5 seconds, 10 seconds, about 20 seconds, about 30 seconds, about 1 minute (min), about 5 min, about 15 min, about 30 min, about 45 min, about 1 hour, up to about 3 hours or more.

As noted above, a training session is a group of trials. A session can contain at least two trials and can contain about 4, about 6, about 8, about 10, about 12, about 15, about 20, about 25, about 30, up to about 40 or more trials. For example, a session can contain about 20 trials. The number of trials in a session can depend on the length of each trial, determined by the user or the program administrator. The length of a session can vary, for instance, it can be about 1 minute (min), 5 min, 10 min, about 15 min, about 20 min, about 30 min, about 40 min, about 60 min, up to about 90 min or more. For example, a session can be about 60 min long. An individual can undergo two or more sessions and as such, there would be an inter-session interval. An inter-session interval can be flexible and chosen by the individual under training. Alternatively, the interval can be pre-determined by an administrator. Some examples include 15 min, 1 hour, 2 hour, 24 hour, 48 hour, 3 days, etc. Alternatively, the inter-session interval can be determined based on user performance.

A group of sessions is referred to herein as a training program. A training program contains at least two sessions over a time period and optionally includes pre- and post-assessment, as described below.

As mentioned above, an individual being trained by the methods of the present invention can follow a variety of routines—training programs. Accordingly, the individual may receive an entire set of trials in a single session, or may receive a trial for a specified number of times each day, a session for a specified number of days, with a specified frequency. In other words, in one training program, the individual may go through a plurality of training sessions with a selected frequency (e.g., 3 training sessions daily) over a period of days or months (e.g., 6 months) to improve cognition, mood or other related effects.

One example of a training program is to carry out one-hour session of trials (each trial lasting about 3 min), three times a week, for four weeks. Another example of a training program is to carry out a 3-minute trial for 12 times in a 24-hour period, 3 times a week, for a month. The methods of the present invention can also be carried out in an ad-hoc fashion without a specific routine. The trials and sessions may be iterated at will with high regularity (e.g. frequently and/or consistently) or low regularity (e.g. sporadically and/or infrequently).

As such, the methods of the present invention can be carried out in a routine and/or program with a flexible range of inter-session and/or inter-trial intervals. From these examples and based on the above, the length of each trial/session/program, the frequency of trial/session/program in any period of a day, week, month, or year, can be selected based on the needs of the individual.

As noted above, during any iterations as represented by step 10 in FIG. 10, stimuli that are presented can be exclusively auditory, exclusively visual, or a combination of both in a session. Similarly, the task involved may also be exclusively tracking (e.g., visuomotor tracking), exclusively target discrimination, exclusively selection, exclusively memory related or a combination of different tasks. Also, the motor responses can be manual, verbal, or a combination of different responses. The types of stimuli and tasks may remain the same within one trial, across trials, within one session, or among two or more sessions. Alternatively, the types of stimuli and tasks can also change from trial to trial and/or from session to session within a specific amount of time (e.g., a day, within a week, within a month or more).

As an example, an interruptor may change across trials or sessions as the type of stimuli to respond. The interruptor can require a motor response in one trial or session, and a word prompt requiring a verbal response in a subsequent trial or session. Such change can occur in response to the performance of the individual on the task, in a random manner, or pre-determined by an administrator. Such change can also occur at the same time a difficulty level is changed or independent of changes in difficulty level. Additionally, the individual can be presented with two or more types of interferences at the same time.

The methods of the invention can also include trials where interference is always absent or where a specific type of interference is continuously present. Similarly, the interference presented can also be exclusively distractors, exclusively interruptors, or a combination of both. Where all the stimuli pertaining to the interference in a trial are exclusively distractors or exclusively interruptors, the interference in a subsequent trial can be a different type of interference than that presented in a pervious trial or a combination. Optionally, the type of interference can also remain the same intra-session (e.g., inter-trial) or inter-session. Accordingly, these and other parameters may be selected to design the methods of the present disclosure.

Difficulty Level

Figure 11:
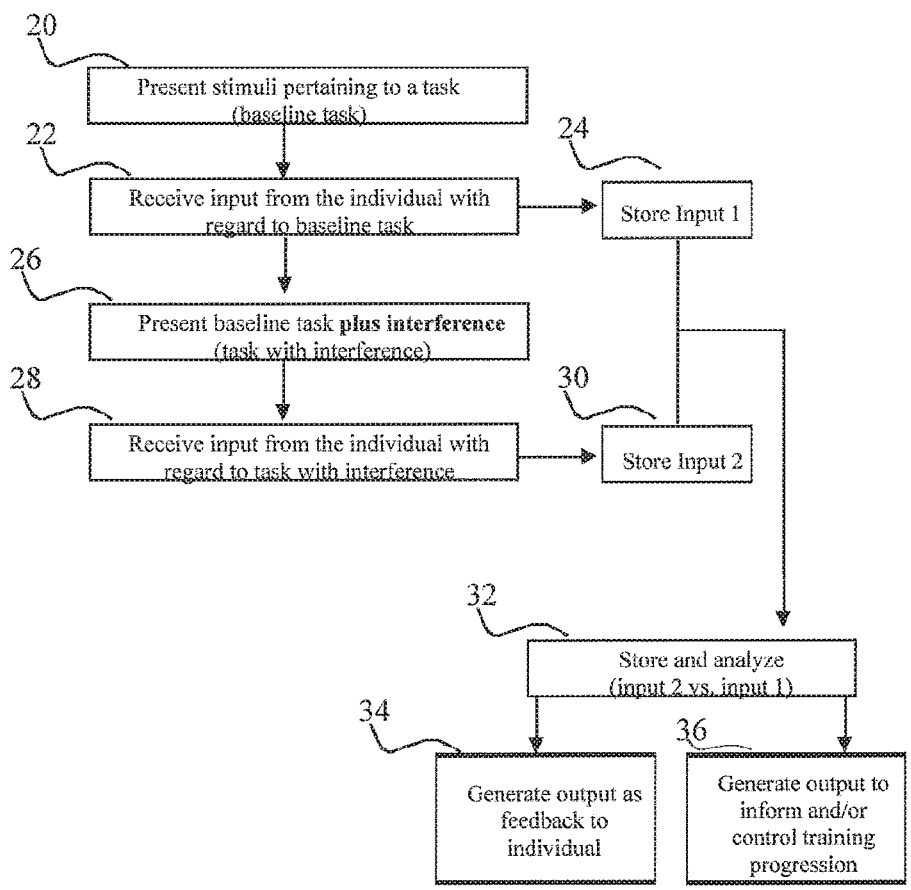
FIG. 11 is a flow diagram illustrating steps of an assessment analysis in accordance with illustrated embodiments of the present invention.

Under the control of system 100, the difficulty level may preferably change or remain the same inter-trial and/or intra-session. The difficulty level of each trial and/or a series of trials in a session can differ among trials and/or sessions. If an individual achieves a threshold level of success (e.g. a pre-determined percentage of correct responses), the difficulty of the trial may be increased relative to the previous trial. Conversely, if the individual achieves a specified level of failure or fails to achieve a level of success, the difficulty of the trial may remain the same or decrease relative to the previous trial. The difficulty level may refer to the task, the interference, or the combination of the two. The difficulty level may also refer to either the actual performance of the task or interference (as determined by input to a task or interference) or a more indirect parameter governed by the analysis of interference cost, as shown in FIG. 11.

A difficulty level can preferably be increased in a number of following ways. In a general sense, difficulty can be increased or decreased along three main modalities: time, space, and identity. An example of time is the window of response to a stimulus, which is the time period between the moment a stimulus is presented and when the input from the individual needs to be received. The individual has this window of time to respond as instructed. Hence, decreasing the inter-stimulus interval, the duration of the stimulus, window of response, or any combinations thereof are ways to increase difficulty. An example of space is varying where in the individual's field of view a stimulus is presented. An example of identity is to select a target based on a categorization of what that target is (for example, its appearance or characteristics). Further examples are provided below.

In a detection task, one way to increase difficulty is to minimize the difference between the stimulus to be detected and the noise and/or background. In a target discrimination task, one way to increase difficulty is to minimize the difference between non-target stimuli and the target stimuli. Images, graphical elements, or auditory elements, can be morphed so that the target stimulus becomes more and more similar (in physical/semantic attributes) to the non-target stimuli. For example, a target of a green circle is more difficult to distinguish from a green pentagon than from a red square. Another way to increase difficulty in both detection and discrimination tasks is to increase the number of elements presented either sequentially or consequentively from which the subject must chose. For instance, increasing the number of shapes from which a subject must select the correct shape.

In an example of visuotracking, as in navigating a car on a winding path, the difficulty level can be increased by increasing the speed at which the car is traveling, the degree of turns, frequency of turns, narrowness of the path, etc. Difficulty can also be increased by increasing unpredictability of the path or blurring the visual stimuli (e.g., provide a fog, obstruction on the path, sudden turns, etc.)

Another way to increase difficulty level is to combine stimuli or tasks that involved different senses (e.g., visual and auditory). Having more than 1, more than 2, more than 3 or more different types of target stimuli in one trial or within a session of trials can significantly increase difficulty. Alternatively, complexity of data processing can also be increased. For example, a task that involves repeating a word in response to a spoken word is less complex than responding to a question. Any one or combinations of these ways to increase difficulty can be used in the methods of the present disclosure.

The difficulty level can be adjusted as frequently as needed and can also be tailored for a predetermined goal or to the ability of the individual. The individual can start at the lowest difficulty level for the first training session of each training period or each day, at the difficulty level determined by assessments, previous training sessions, or at the difficulty level of his choosing. The individual may be presented with the same difficulty level sessions until a certain level of success or failure is reached. The difficulty level can also decrease, increase, or remain the same, regardless of the performance of the individual. For example, the training may design to have difficulty levels that change in a stepwise fashion or increases and decreases in peaks and valleys so to provide variety, challenges, or interest to an individual. These pre-designed plans of difficulty levels can be independent, or partially dependent on the performance of the individual.

The methods can also be specifically tailored to the individual by maintaining around a threshold success rate for the individual. For example, the methods can be tailored to target a constant error rate from an individual (e.g. approximately 80% response accuracy).

Termination

The steps in the methods of the present invention in accordance with the illustrated embodiments can be repeated in a trial and the trials are repeated in a session to achieve a predetermined goal. Sessions are repeated in a period of time to constitute a training program. A predetermined goal may be dependent on the responses of the individual or the length of the training. For example, the goal may be for the individual to undergo trials with a certain frequency for a specific length of time (e.g. a month). Alternatively, a sessions can repeat as many trials as necessary or a program can repeat as many sessions as necessary to train the individual to perform at a certain level, measured by one or more indices, e.g., only true hits and no false positives, a certain percentage of true hits, inputting true hits consecutively for a number of times, or a specified reduction of multitasking or distraction costs, or improvement in another cognitive measure that has been obtained prior to training (such as working memory, long-term memory, task-switching abilities), etc.

The number of iterations that occur in a trial before termination can be based on a number of factors. One is the performance of the individual, as noted above. The iterations can terminate as see in step 14 in FIG. 10 when the individual performs with a high level of percent accuracy for a pre-determined amount of time (e.g., 80% f or more). Alternatively, the iterations can terminate to conclude a trial when the individual has committed a number of errors. Another factor is the amount of time for which a particular individual or an average individual can concentrate in performing the task. As for terminating a session, the factors involved in determining the number of trials in a session before termination are similar to those involved in a trial. As an example, the session may terminate regardless of the correctness of the inputs in the various trials after a select duration of time (e.g. about 5 trials, about 10 trials, about 15 trials, about 20 trials, up to about 30 trials, or more). Termination may also be determined by the individual who may set either the time, the number of iterations or may have the option of terminating the trial independent of the number of iterations or time.

As for a training program, a training program, for example, may repeat as many sessions as is necessary for the individual to attain at a level of proficiency in which the car can be navigated in the center of the path at least 80% of the time, while simulataneously responding to the target discrimination task. In a target discrimination task in the setting of distracting auditory stimuli, the training sessions can repeat until the ratio of true positives (hits) to false positives achieves a selected threshold. For example, the training may terminate when true positives/negatives significantly outweigh the false positives/negatives in the last 5 sessions. A combination of the thresholds or factors can be analyzed in an assessment to determine the duration of a training program and when termination should occur. Details of an assessment are discussed below. Alternatively, a training session can be terminated by a program administrator and/or the individual at will.

Before a First Session

The individual may be participating in the methods for the first time. A first time refers to a first participation in his life or a first in an experimental period (e.g., one month). Alternatively, a first time can also refer to an individual participating in the method for the first time of the day. Alternatively, a first time can also refer to an individual participating in a method that is substantially similar but has slight variations from what the individual has participated in in the past, whether in the long-term past or in the immediate past.

It would also be appreciated that the method can encompass a step prior to the first presenting step. Where the method is carried out for the first time for an individual, the method can optionally encompass a thresholding step, an assessment, instruction, and/or demonstration. See FIG. 12 as an example of a system containing an assessment step before and after a session or training program.

A thresholding step includes presenting an individual a task without interference in one or more trials. This thresholding step helps determine how an individual performs the task without interference. Another purpose of the thresholding is to determine a difficulty level to carry out an assessment and other steps of the present method. Thresholding to a specific difficulty level can be useful in tailoring the present methods to an individual because each individual can have variable baseline abilities to perform a task without interference (e.g., older adults can perform a variety of tasks at a lower performance level when the task is matched in difficulty). If thresholding is not performed, the presence of an interference can place a different demand on the individual depending on his baseline level. Normalizing each individual to a difficulty level can result in a standardized level of interference that is independent of baseline performance on level on the task.

A difficulty level to carry out an assessment or other steps of the methods is a level at which the individual performs the task with a pre-determined percentage of accuracy (e.g., 80%). The difficulty level of this task without interference can be first presented at a difficulty level that is a default for a category of individuals (e.g. average for an age range), a lowest level of difficulty, or a level comparable based on the individual's prior assessment. The difficulty levels then can change until the individual performs with a specific level of accuracy. In an alternative method, a single training session run can use adaptive thresholding methods (such as psychometric staircase algorithms) to quickly threshold the individual at a specific performance level.

Accordingly, the threshold level can be personalized to the individual. For example, a threshold level for the first time is a level at which the individual can perform the task without interference with an accuracy of about 50%, about 55%, about 60%, about 65%, about 70%, about 75%, about 80%, about 85%, or about 90% or more. After a thresholding step, the method of the invention may include an assessment before and/or after a training session or training program. Details of assessment are discussed later below.

Before the beginning of a training session, the methods can optionally demonstrate the type of task and stimulus to be presented and instruct the users how to input a response prior to running a trial. Instructions can provide an exercise to familiarize the individual with the procedures of receiving the presentation of stimuli and with the procedures of inputting a response. The instruction can include details on the types of responses expected from the individual when presented with the stimulus/task or in the absence of the target stimulus. The response can be a physical action of clicking a button and/or moving a cursor to a correct location on a screen, head movement, finger or hand movement, vocal response, eye movement, foot pedaling, running on a treadmill, jumping, etc. Input or response from an individual received by the methods of the present disclosure involves a voluntary initiation of an action on the part of the individual and excludes measurements that may be obtained from an individual passively. In some embodiments, passive inputs, such as brain waves, such as those obtained in magnetoencephalography, are excluded as an input from an individual in the present disclosure. In other embodiments, the methods can encompass receiving as inputs, both a voluntary action on the part of the individual and one or more passive measurements. Passive measurements can include any physiological recording, such as electroencephalograph (EEG)/functional magnetic resonance imaging (fMRI)-style measurements, galvanic response, heart-rate, heart-rate variability, etc.

Response and Feedback

As noted above, the method of the invention according to the illustrated embodiments assign an individual a task that involves responding to a series of stimuli. Depending on the task, an individual can respond in one or more of a variety of ways, including but not limited to vocally or via his or her motor function. For example, in a target discrimination task, the response is to click a certain button when presented with a target stimulus and refrain from clicking the button when presented with a non-target stimulus. Other motor response can include, but are not limited to, stepping on a foot pedal, moving another part of the body (e.g., nodding), running, jumping, etc. Alternatively, the individual can respond vocally by speaking a word or a phrase when presented with a target stimulus.

Where the task involves a series of visual stimulus as a motion picture, the individual may be instructed to navigate a moving object such as a vehicle (e.g., a car or a bike) or to click on certain moving objects. These types of response may be described as visuomotor tracking and can be performed with a keyboard, joystick, bicycle, treadmill, or other exercise equipment, for example. Similarly, where an individual tracks an auditory stimulus by clicking in the direction of the source of the sound, the response may be described as auditory-motor tracking.

The following are types of responses that can be received from the individual: Hit (true positive): If the individual correctly indicates the presence or absence of one or more target stimuli, the response is considered to be a hit. The response would also have to be received within the window of response. For example, the response could be an input via a user interface into a computer, remotely or locally. When the individual's response is a hit or true positive the individual may receive a feedback or output.

Non-response (true negative): If the individual correctly refrains from indicating the presence of a target stimulus in a stimulus set, i.e. due to the absence of a target stimulus, the individual's response is a non-response or true negative. The individual may be rewarded an output as described above for true positives.

False positive (false alarm): if the individual incorrectly identifies that a non-target stimulus as the target, the individual's response is a false positive. In this case, the individual may receive a penalty as an output.

Miss (false negative): If the individual incorrectly failed to indicate the presence of one or more target stimuli, the individual's response is a false negative within a window of response. The subject may be penalized as described below with a bonus meter reset (where progress toward a bonus is reset to zero or decreased).

If the response is unclear such that it cannot be categorized by the computer or other tools carrying out the subject method, the response can be categorized into false positive, false negative, or simply as an uncategorized/undetermined response.

Where the task involves tracking (e.g. visuomotor tracking), such as navigating a car on a winding path. The response can be evaluated as the percent of time the object remains on or near the center of the road (hits) and the percent of time the object encroaches beyond the boundary of the path (misses).

Where the feedback is generated in response to an input during a trial, the feedback pertains to real-time performance of the individual during a session. Where the stimulus is visual, frame parameters may change, i.e., the graphical user interface (GUI) may modify the color of the region around the target stimulus or stimulus set to indicate an error. For example, in a task requiring navigation of an object such as a vehicle on a winding path, there may be a shape (e.g., a crosshair) that appears above or in the same visual field as the vehicle that changes color, vibrates, etc., in response to how well the individual is performing. Likewise, the object being navigated itself might change to provide the subject feedback on performance (e.g., change color). If the vehicle is in the center of the path, a crosshair may be green and steady. If the vehicle encroaches the boundary of the road or go off path, the crosshair may shake or change to a red color.

Other feedback during a trial may be used as desired, e.g., visual shapes, e.g., an "X" in the corner of a screen, resetting the bonus meter, and so forth. Either an auditory or a visual output may also inform the individual a score that has increased, decreased, or remained the same in the number of points, as an indication of whether the input is correct or not.

Difficulty levels can also be changed in real-time as feedback. Difficulty can increase or decrease in relation to the performance of the task (e.g., a car becomes more or less sensitive to controller manipulation when there is progress in the performance of a task. The car can also become more or less sensitive to controller manipulation when there is negative progress. Other changes in difficulty level encompass darkening all or partial screen view or brightening or clearing up the visual view. For an auditory stimulus pertaining to the task or interference, similar strategies may be used. These examples and other ways of changing difficulty levels described above can be a mode of feedback to the individual.

As seen above, the method can generate an output to inform the individual whether or not the input is correct. Both the output and the stimuli can be exclusively auditory or exclusively visual. Alternatively, the output can be auditory if the task involves visual stimuli and vice versa in order to avoid confusion. Some examples of outputs are discussed below.

After a series of inputs (e.g., after termination of a trial or a session of trials), the methods store and/or analyze the inputs to determine how well each task is performed. The method can optionally generate an output to inform the individual of the performance level for the completed training session. The output may be auditory feedback, such as sound (e.g., a "thunk" or silence for a decrease in performance and a "ding" for an increase in performance level relative to a previous trial) or visual feedback (e.g., a graphical indication). Output can include bonus meter advances, and after five non-responses in a row, for example, visual feedback (e.g., a graphical success indication, progression of levels, such as a displayed "checkmark"), lack of point addition or subtraction of points and/or addition of points.

The output at the end of a complete trial or a training session can further include an in-depth analysis. The analysis consolidates all or part of the indices measuring the performance of the individual. The data used for the analysis may be derived from the training session itself and/or a post-training assessment step as discussed below in further detail.

Pre-Training and Post-Training Assessment

As noted above, methods of the present disclosure can further include a pre-training assessment and a post-training assessment. A simple way in which this fits into the global training process is demonstrated in FIG. 12. The methods can also include one or more of the assessments intermittently throughout the training in order to provide feedbacks as discussed above (e.g., inter-trial or inter-session).

Similar to other steps in accordance with an illustrated embodiment of the methods of the invention described above, an assessment can include presenting a task and optionally an interference to an individual, and evaluating the performance of the individual with and/or without the interference. An assessment is different from a training session in that it does not seek to train the individual. In one embodiment, unlike a training session, the difficulty level from trial to trial in an assessment does not change or adapt to the performance of the individual. Rather, the difficulty level in an assessment trial remains the same (e.g. at the difficulty level determined by the thresholding step). In another embodiment, the assessment does adapt in the training session, by methods known in the art of psychometric analysis such as staircase procedures and maximum likelihood procedures to adaptively determine the ability of the participant. In either case, the purpose of the assessment is mainly to evaluate the performance of the individual as opposed to train that performance. In one illustrative embodiment of the methods of the present invention, the pre- and post-assessment are generally conducted as described above and in FIG. 11.

As a specific example, an assessment can include presenting a target discrimination task in the presence or absence of an interference, such as an interruptor or distractor (e.g., car driving autopilot in the background). An assessment also may present a trial including a visuomotor tracking task in the presence of an interruptor or a distractor. An assessment can contain about 2, about 3, about 4, about 5, about 6, about 8, up to about 10 or more trials. Each trial can differ in the task and/or interference presented. An assessment can include a series of trials that last about 20 min, about 30 min, about 40 min, about 50 min, up to about 60 min or more. For example, an assessment may be a series of five different trials conducted within a 60 min period.

Referring to FIG. 11, the assessment described above can be conducted before and/or after a training session or training program. The steps involved in a post-training assessment are the same as those of a pre-training assessment described above, except that in a pre-training assessment, the data are used to determine the ability and/or performance of an individual prior to training. In a post-training session, however, the data analyzed may include data collected not just in the assessments themself but also during the training program. Additionally, the post-training assessment may be used as feedback to the individual, as well as feedback to the training program, as a control by which to direct the advancement of the next training session.

The analysis also reflects the performance and ability of the individual after training. In other words, post-training assessment can compare the performance of the individual post-training to that prior to training and assess the impact of training on the cognitive ability of the individual. See FIGS. 5A-5B for example.

In some embodiments, the pre- and post-training assessment tests functions that are essentially the same as the task and/or interference being trained, and thus provides a direct measure of an individual's performance increases in that specific environment. In other embodiments, the pre- and post-training assessments are different than the task or interference, and thus test if a transfer of benefit of the training session or program has been achieved. More detail is provided in the Demonstration of Efficacy section below.

Where the methods of the present disclosure include a post-training assessment step, a variety of data and analysis can be carried out. The data analyzed may include percent accuracy, hits, and/or misses in the latest completed trial or training session. Another index that can be used to measure performance is the amount time the individual takes to respond after the presentation of a target stimulus. Other indices can include, for example, reaction time, response variance, correct hits, omission errors, false alarms, learning rate, and/or performance threshold, etc. The performance can be further analyzed to compare the effects of two different types of interference (e.g. distraction or interruptor) on the performances of the various tasks. Some comparisons can include performance without interference, performance with distraction, and performance with interruption. The cost of each type of interference (e.g. distraction cost and interruptor/multi-tasking cost) on the performance level of a task is analyzed and reported to the individual. For example, an individual can be informed that his performance level decreased 10% in the presence of a visual distractor (distraction cost), but decreased 20% in the presence of an interruptor (e.g. when he is multi-tasking) (multitasking cost). As such, the cost of the distractor is half as much the cost of multi-tasking.

Any or all of the analyses and data may be presented to an individual in a report listing the task, the specific type of interference and their corresponding cost to each task. The methods can also generate a report with a graph showing any previous session or series of session in comparison to the latest session. The analysis may further categorize performance based on the type of stimuli and sensory functions involved in the tasks or interference. Additionally, the analysis may present the performance measures relative to another group (e.g., how a particular individual compared to others in his age range). These and other analyses can be reported directly on a display screen, stored in a database, and communicated audibly and/or via electronic mail as well as other electronic means.

As noted above, aside from determining the correctness or incorrectness of the individual's response, the method can also analyze, store, and output the reaction time for the response and/or any statistical measures for the individual's performance (e.g., percentage of correct or incorrect response in the last number of trials, over a specified duration of time, or specific for a type of non-target and/or target stimuli, a specific type of task, etc.). In addition to what is discussed above, other means of assessing the cognitive abilities known in the art may also be employed as a post-training assessment or part thereof.

Some examples of assessment of cognitive abilities known in the art include those for intelligence (e.g. Kohs block, Miller Analogies Test, Wechsler Adult Intelligence, Wonderlic Test, or other IQ-related test), for cognitive development (e.g. Knox Cubes, language aptitude, Porteus Maze Test, and the like), psychiatric/personality test (e.g. Myer-Briggs, etc.), and memory test (e.g. short-term, long-term, working, semantic, etc), sustained attention test, selective attention tests, Useful Field of View, TOVA, Filter test, Object-tracking test, dual-task test, attentional blink The one or more different outputs of described above may or may not be presented to the individual after each trial. When and what output is generated can also be pre-determined by the individual and/or the operator of the training program.

In addition to providing an evaluation on the performance of the individual and the impact of a training, assessments can also be used to guide an ongoing training program. Periodic assessments over time can be used to determine if there is need to alter or maintain a particular strategy for training e.g. maintaining/changing a task, an interference, a particular type of stimuli, means of input, etc. For example, an assessment may inform a program administrator that the individual in need for a "booster" training. Such assessment can be carried out inter-trial, inter-session, or in between administering two or more training programs. See FIGS. 11 and 12 as an example where multiple arrows reflect the flexibility of inserting assessment wherever appropriate as part of an ongoing process. The combination of the iterative nature of the training and assessment is an example of a system approach to the methods of the present disclosure.

The methods of the present disclosure may also be combined with other methods that aim to enhance cognition or methods that improve physical fitness, and overall wellness. For example, the training of the methods of the present disclosure can alternate or can be employed concurrently with training of a second method to result in a combination training regimen. One example is to require inputs from individual that involve physical exercise, such as running on a treadmill, bicycling, using a device with motion/position sensor technology (e.g., Sony Wii Fit, Playstation Move, or Xbox Kinect), and the like. The physical exercise as input may be unrelated to the task or interference presented to the individual. Alternatively, the physical exercise may be the means by which the input is received to perform a task.

The method may be designed to be presented to an individual in a form of game or challenge, in which instructions to an individual include game objectives and individual's input are scored. For example, a correct response increases points whereas the score remains unchanged or decreased in points if the response is incorrect.

The methods of the present invention encompass the addition of engaging game elements that are integrated with the training session. These game elements confer substantial benefits to the user or the training program. One benefit is that the game context may encourage the user to engage more attentional resources to task, which can be critical for enhancing cognition. Additionally, the game context can provide incentives for a user to pay attention and/or complete the training. In other words, the interest and goal orientation created by the game context provide incentive to continue training for longer periods of time than would generally be supported by the less engaging training task on its own. Game specific features that can increase incentive and interest of an individual may include but not limited to bonus points, in-game reward or penalty, such as a graphical or auditory representation thereof, rewards or penalties that scale with difficulty level or time spent, real life rewards, etc. Additional game elements to enhance engagement are common to those skilled in the art of video gaming, board games, cognitive paradigms, fitness/sports instruction, and educational programs.

Diagnostics

As noted above, the method optionally includes a pre-training assessment and/or a post-training assessment. In addition to being employed to to evaluate an individual for training purposes, the assessment can be used alone or in combination with other regimen (e.g. physical wellness or medical treatment) for diagnosis purposes. Regardless of whether the assessment is used for a training program or for a diagnosis of a specific condition or clinical disease, the same type of assessment can be used. One example is the type of assessment diagrammed in FIG. 11.

Steps of an assessment as described above provide a measure to evaluate the effectiveness of training. As described above and in the example section below (of this FIG. 6), an individual's distraction and multitasking costs can be measured and compared to those prior to training.

In dependent of the training, assessment can also be used in other contexts, such as to assess an individual for its cognitive ability to diagnose disease or prognosis. Cognitive ability (e.g., susceptibility to interference, working memory, multi-tasking ability, and the like) provides an important index in diagnosing diseases related to cognitive impairment (e.g., Alzheimer's disease), side-effects of drug, surgery, or other medical intervention, prognosis, etc. Target populations for training and/or diagnostics are described in greater detail below.

Stimulus

As noted above, the method involves presenting to an individual a task in addition to an interference. A task involves presenting a stimulus that requires a response from the individual as an input. An interference involve presenting one or more stimuli that are to be ignored (i.e., a distractor) or that require a response (i.e., an interruptor).

A stimulus employed by the present methods may be visual or auditory, for example. A task further requires a response from an individual that may require data processing and commands of certain senses. Below are descriptions of some examples of stimuli that can be used in the present methods and the senses involved in generating a response in a task.

Visual

A stimulus presented to an individual can be visual. A visual stimulus is made up of electromagnetic waves in the visible light spectrum and may be characterized by, for example: brightness, color, shape, surface texture, orientations (e.g. grating), location in a visual field, orthographic (e.g. textual), quantity, or motions, as well as properties of these characteristics. Each stimulus may also be referred herein as a graphical element.

Each graphical element may be presented with a specific duration to an individual, e.g. for a fraction of a second, for a second or for a length between about 1 and about 2 seconds or for up to about 2 seconds or more. For example, a visual stimulus may be a geometric shape of a circle, or a red cone, the number "5", or the like. Another example of a visual stimulus can be a specific human face, face of a specific age range, face of different ethnicities, or any parametric variations thereof.

A visual stimulus can also be an image that is rich so as to contain multiple shapes, colors, textures, etc, as seen in a photograph, digitally-generated picture, or moving video such as in current movies or video games. The image may be a vehicle advancing on a road, in which the road can be of various shapes and width. A series of consecutive images can be presented so the individual would perceive the visual stimuli in a form of a motion picture. In the example of an image of a vehicle on a road, a series of visual stimuli can present to an individual a vehicle that is advancing on the road.

Where the visual stimuli are employed in a task, the task can be target discrimination for example. The task may involve instructing an individual to respond to a green circle whenever a green circle appears on the screen. Where other shapes or other colored circles are presented (e.g. green pentagon), the individual is not to respond. How an individual may respond in a task is discussed later below. A target visual stimulus can also be a face of a child while the non-target stimulus is a face of an adult. As another example, a target visual stimulus can also be a visual image of a first animal (e.g., non-human animal) of a certain species while the non-target visual stimulus can be an animal of a species different from the first animal. A target visual stimulus may differ from a non-target visual stimulus in one or more of any properties inferred from herein.

The visual stimuli can also be presented in another type of discrimination task. The individual is presented a series of visual graphical elements and is instructed to respond to a target graphical element that does not belong in the same category as other non-target graphical elements in the series. In another similar task, the individual can be instructued to identify a part that does not appear in a correct location or orientation as other parts of an object that are presented to the individual in a series.

Where the task involves images presented as a motion picture, the task can involve visuomotor control. The individual would be instructed to control a moving object in an environment in which the colors, shapes, or any properties discussed above are changing. One example includes navigating a moving vehicle on a winding path or on a path with obstructions. Other examples can include clicking on specific objects that appear or move.

Auditory

A stimulus presented to an individual can be auditory. An auditory stimulus refers to a sound and may be characterized by, for example: frequency, loudness (i.e. intensity), timbre, or any parametric combination of these or any other sound features. The duration of time an auditory stimulus is presented to an individual can be varied. For example, an auditory stimulus may be presented to an individual, e.g. for a fraction of a second (such as about 40 milliseconds (ms), about 50 ms, about 60 ms, about 70 ms or more), for a second or for a length between about 1 and about 2 seconds or for up to about 2 seconds or more. An example of a duration of an auditory stimulus presentation is about 100 ms.

A stimulus can also be spectrally-complex stimuli like vowels, phonemes, syllables, words, questions, or statements. A stimulus can also be presented by a voice and as such characterized by the presenting voice (e.g. call of a specific bird). The auditory stimulus can also be characterized by a waveform that is defined by amplitude (i.e. intensity or loudness), frequency, or any other sinusoidal properties.

Similarly to the visual stimulus discussed above in which a series of visual stimulus is perceived as a motion picture, a series of auditory stimulus can be perceived by the individual as a statement, a song, a narration, etc.

Where the task involves target discrimination, a target auditory stimulus can differ from a non-target auditory stimulus in any one or more of the characteristics, such as frequency, loudness, or timbre, as well as properties of these characteristics. For example, if they differ in frequency, the difference in frequency may be measured in hertz or octave. Hertz (Hz) measures the numbers of cycle per second in the sound wave while octave represents frequency as pitch. The frequency difference between a non-target auditory stimulus and a target auditory stimulus may be between about 0.01 to about 0.05%, between about 0.05% to about 0.1%, between about 0.1% to about 0.3%, between about 0.3% to about 0.5%, between about 0.5% to 1%, between about 1% to about 3%, between about 3% to about 6%, up to about 9% or more.

Where the difference between a non-target auditory stimulus and a target auditory stimulus differs in loudness, the difference can be expressed in sound pressure level (SPL) measured in decibels (dB) above a standard reference level. The standard reference level is about 20 μPa. For example, in a target discrimination task, an individual can be instructed to respond to only to a female voice.

In another task that involves auditory stimulus, the individual can be instructed to answer a question that is asked vocally or to repeat certain words or sounds in response to a spoken auditory stimulus.

Any of the characteristics of sound described above, and combinations thereof, can be one or more of the ways in which the target auditory stimulus may be used in the present methods.

Combination Stimulus

A combination of stimuli of different sensory systems may be presented to the individual in the methods of the invention in accordance with the illustrated embodiments. For example, both auditory and visual stimuli may be presented concurrently or in sequence. The series can also present a sequence of auditory and visual stimuli that can be synchronized or unsynchronized. In a discrimination task, a target set can contain either a target auditory or a target visual stimulus or both. For example, a target stimulus may be a combination of the visual stimulus of a green circle as well as the spoke word "circle" as the auditory stimulus.

Timing of Presentation

During iterations, two or more interferences can be presented and the interference can be presented in a variety of different sequences and timings. Using various sequences and spacings of interference can train the desired effects of the invention in multiple ways, and may have different effects for different users. For example, the interrupteors and/or distractors can be presented rapidly, or very sparsely, or in random spacings. Interruptors and distractors may alternate in regular patterns or may vary with a random interval with respect to a previous interference or a stimulus pertaining to a task. As noted above, interference can be presented concurrently or sequentially with a task. For example, an interference can be presented during an interval between stimuli pertaining to a task. Either the individual or the program administrator can control the jitter of the timing between the interference and the task.

Two or more stimulus pertaining to a task or interference can be presented in a series (e.g. a motion picture or a sentence). A sequence of stimuli presented to an individual with the same or similar inter-stimulus-interval (ISI). Where the sequence of stimuli is presented to an individual with the same ISI, the stimuli are said to be occurring in the same frequency in a session. For instance, the ISI of a set can be 3 seconds (s), 2.5 s, 2 s, 1 s, or a fraction of a second, such as about 600 milliseconds (ms), about 500 ms, about 400 ms, about 300 ms, about 200 ms, or about 100 ms or less. Alternatively, the series of stimuli may not have the same ISI and the ISI may be random.

Where a visual stimulus set is presented as a motion picture, ISI of consecutive images can also be referred as frequency and can be expressed as frames per second (FPS). For instance, a motion picture can have a frequency of about 40 Hz, about 45 Hz, about 50 Hz, about 55 Hz, or about 60 Hz, about 70 Hz or more.

Where there is a discrimination task, the set contains a target stimulus, the set contains at least one target stimulus in the sequence. The percentage of target stimulus can vary, such as, but not limited to, about 10%, 20%, 40%, 50% or 60% or more of the non-target stimuli presented. The number of target stimuli can be less than the number of total stimuli. Alternatively, the percentage of target stimuli can be random. The target stimulus can be presented in a constant frequency or random in a series. For example, the target stimuli can have an equal chance to appear at any location in a series of stimuli or consistently every 3 stimuli.

Target Population

Individuals that can use the methods and tools of the invention can be any person, especially those interested in enhancing cognitive abilities. For any of the target populations described below, diagnostics to assess one's cognitive ability (e.g. impairment or susceptibility to interference) and training are particularly useful applications of the methods of the present disclosure. It is becoming recognized in the cognitive field that interference in cognitive function severely impacts cognitive performance across a range of functions, including perception, attention, and memory. Accordingly, there are many potential populations that would benefit from a new training method that specifically aims to enhance the ability to deal with interference.

Individuals that can benefit from the subject methods and tools include but not limited to adults, such as aging adults. For example, the subject methods and tools can be useful for adults that are of any age. It is well-known that healthy aging adults have a significant deficit in processing of cognitive interference. Additionally, findings of the present invention show that even young adults can show signs of such a deficit. Therefore, as examples, adults of about 30 years old, about 40 years told, about 50 years old, about 60 years old, about 70 years old, up to about 80 years old or older may be an individual to the methods of the present invention. Measurable deterioration of cognitive abilities in an individual is common as he or she ages. The experience of this decline may exhibit as an occasional oversight in various tasks and/or increasing difficulty in concentration. The decline often progresses to more frequent lapses as one ages in which there is passing difficulty performing tasks requiring extraction of visual or auditory information while multitasking or avoiding distractions. Avoiding dangers when driving a car, scanning a crowd for a familiar face, and reading quickly are a few of such examples. Thus, the present invention is particularly useful in individuals of any age desiring to improve their cognitive abilities or ameliorate an established decline or the rate of decline in cognitive function.

Such decline typically accelerates at age 50 and older and over subsequent decades, such that these lapses become noticeably more frequent. It is often clinically referred to as "age-related cognitive decline." While often viewed (especially against more serious illnesses, such as Alzheimer's disease, Parkinson's disease) as benign, such predictable age-related cognitive decline can severely alter quality of life by making daily tasks arduous.

Age-related cognitive decline can lead to a more severe condition now known as Mild Cognitive Impairment (MCI), in which sufferers show specific sharp declines in cognitive function relative to their historical lifetime abilities while not meeting the formal clinical criteria for dementia. The subject methods and tools have the potential to reverse and/or prevent the onset of this devastating neurological disorder in humans, such as those suffering or at risk for MCI.

Aside from age-related cognitive decline, people of all ages who experience or are at risk for cognitive impairment can benefit the present invention. For example, the present invention is useful for training individuals whose cognitive losses have arisen as a consequence of injury (e.g., traumatic brain injury), medical treatments, chronic neurological, psychiatric illness, or of unknown cause. Such cognitive impairment, age-related or not, can be a contributing factor or manifesting symptom of a variety of conditions, including Alzheimer's disease, Parkinson's disease, Huntington's disease, depression, schizophrenia, dementia (including, but not limited to, AIDS related dementia, vascular dementia, age-related dementia, dementia associated with Lewy bodies and idiopathic dementia), Pick's disease, cognitive deficit associated with fatigue, multiple sclerosis, post traumatic stress disorder (PTSD), obsessive-compulsive disorder (OCD), and others. Other cognitive losses can include brain damage attributable to infectious pathogens, medical intervention, alcohol or drugs, etc. Thus, cognitive decline or impairment can be a contributing factor or negative influence on a variety of adverse conditions, and thus the present invention can be useful in combating or diagnosing anxiety, stress, panic, depression, dysphoria, or malaise. Additionally, cognitive decline may result as a secondary symptom from a variety of disease states that are on the surface unrelated to cognition, but which significantly adversely affect the above-mentioned cognitive processes. Accordingly, individuals experiencing pain or diseases having a significant pain component, insomnia, or adverse effects of disease treatment such as chemotherapy or radiation therapy can also find use in methods of the present disclosure.

Populations that can benefit from the present methods further encompass those that suffer from attention deficit disorder (e.g. attention deficit hyperactivity disorder (ADHD)). Cognitive losses of developmentally impaired child and adult populations, encompassing general or undiagnosed developmental delays, Autism Spectrum Disorders (ASDs) (e.g. Aspherger's), can also be potentially reversed by the subject method.

For individuals suffering from chronic neurological and psychiatric illness, changes in inhibitory neuron populations, myelination, response slowing, emergent response dis-coordination, degradation of response selectivity in spatial, spectral and temporal detail, and the degradation of the distinctions between background and target stimuli are very similar to the effects of age-related cognitive decline. Accordingly, individuals of any age with profiles of cognitive impairment that parallel those in aging are target populations for the methods and tools of the present disclosure. The individuals can experience substantial 'corrective' neurological changes if trained by the subject methods.

Additionally, many individuals, though not experiencing a perceptible decline in cognitive function, may desire to increase their current cognitive abilities. One example is to improve the performance of everyday tasks (e.g. multitasking, focus, memory, social skills, such as conversational skills, decision-making abilities, creativity, or reaction times to specific task). Another example is to improve general metrics of cognitive ability (e.g. to "enhance IQ"). Since people are susceptible to interference or are exposed to interference in daily life, the present methods also have a utility for training cognitive abilities in those who are not necessarily experiencing a cognitive decline or impairment. Secondary effects dependent on the above mentioned and trained cognitive abilities may also be a target for training using the present invention. Examples include learning, such as learning in a specific subject area (e.g. math or reading), a general ability to learn in the presence of interference, enhancing social interaction, etc. Therefore, regardless of performance level, pre-school and school-aged children, and teenagers and young adults would be key populations that could also benefit from the interference training as described herein. Furthermore, populations whose activities involve multitasking could increase performance in carrying out their professional duties or hobbies. Examples of such populations include, but are not limited to, athletes, airline pilots, military personnel, doctors, call center attendees, teachers and drivers of vehicles.

Demonstration of Efficacy

With the goal to diagnose or enhance cognition and related effects in individuals, it can be desirable to experimentally determine the efficacy of a training session or program. Suitable methods of experimental testing include those types of studies known in the art to test the efficacy of cognitive, behavioral, or pharmacological intervention, including pilot human studies and clinical trials. These types of experimental tests can be conducted with any group of individuals, and preferably with a group of individuals that represents the target population of the eventual training session or market products. Preferably, the studies are conducted in such a way as to give strong statistical powering to the conclusions, including methods known in the art such as placebo/sham/vehicle comparator groups, blinding of subjects and experimenters, randomization of subjects into the various groups, and the like.

Figure 12:
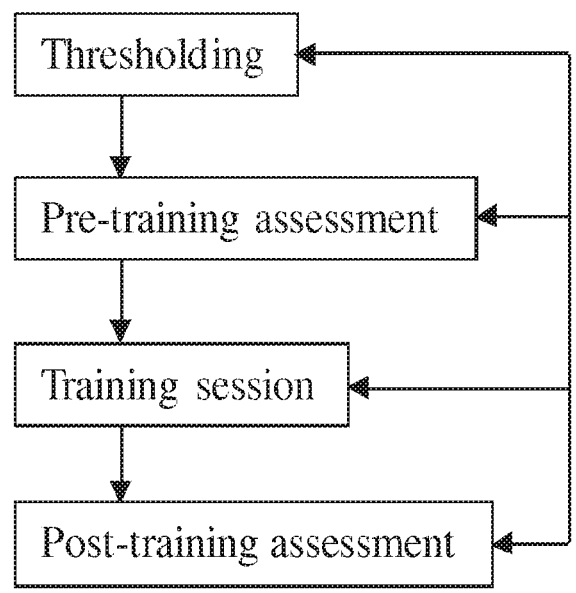
FIG. 12 is a flow diagram illustrating an entire training process in accordance with illustrated embodiments of the present invention.

As mentioned in sections above, one efficacy-testing method suitable for the present invention is the administration of pre-training and post-training assessments which allow for the determination of whether training has led to a measurable change in the function of which the assessment is composed. The general outline of such a testing procedure is shown in FIG. 12. Assessments can be comprised one or more of a variety of types of functions.

In one embodiment, the pre-training and post-training assessment is comprised of general cognitive functions, which pertain to both healthy individuals and individuals that have experienced or are at risk of experiencing cognitive deficits, including clinical patient populations. Such suitable tests include those known in the art to test any specific functions of a range of cognitions in cognitive or behavioral studies, including tests for perceptive abilities, reaction and other motor functions, visual acuity, long-term memory, working memory, short-term memory, logic, decision-making, and the like. Specific examples of such measurements include but are not limited to TOVA, MOT (motion-object tracking), SART, CDT (Change detection task), UFOV (useful Field of view), Filter task. WAIS digit symbol, Troop, Simon task, Attentional Blink, N-back task, PRP task, task-switching test, Flanker task.

In another embodiment, the pre-training and post-training assessment is comprised of tests that measure improvement on actual functional activities of daily living. Examples can include tests that are specifically constructed or validated to measure such outcomes, such as Activities of Daily Living that are used in clinical trials of elderly populations, or similar simple measurements such as the ability to perform a directed task, reading or conversational comprehension, efficiency in a workplace environment, and the like.

In another embodiment, the pre-training and post-training assessment is comprised of tests that measure improvement on symptoms or functions relevant to a specific disease or condition. Suitable types of tests include those that objectively measure symptom severity or biomarkers of a disease or condition, tests that use subjective clinician or observer measurement of symptom severity, and tests that measure cognitive functions known to be correlated with disease states. Examples of such tests include but are not limited to assessment scales or surveys such as the Mini Mental State Exam, CANTAB cognitive battery, Repeatable Battery for the Assessment of Neuropsychological Status, Clinical Global Impression scales relevant to specific conditions, Clinician's interview-Based Impression of Change, Severe Impairment Battery, Alzheimer's Disease Assessment Scale. Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale. Aberrant Behavior Checklist, and Activities of Daily Living scales; physiological tests that measure internal markers of disease or health such as detection of amyloid beta, cortisol and other stress response markers; and brain imaging studies (for example fMRI, PET, etc.) that assess a condition based on presence of specific neural signatures.

In another embodiment, the pre-training and post-training assessment is comprised of survey or questionnaire-styles test that measure a subject's self-reported perception of themselves. These can include self-report scales of healthy function or feelings, or disease function or symptoms. Examples of suitable self-report tests include but are not limited to ADHD self-report scale, Positive and Negative Affect Schedule, Depression Anxiety Stress Scales, Quick Inventory of Depressive Symptomatology, PTSD Checklist, and any other types of surveys that can be conducted for a subject to report on their general feelings of symptoms of a condition or satisfaction with real-world functional status or improvement.

End-User Products

The present invention can be incorporated into a variety of manifestations that deliver the training to an individual, including "products" that would be used by individuals of the target populations. Such products may be provided by a cognitive scientist or researcher, a clinician or other health-care provider (such as a psychiatrist, psychologist, physician, nurse, or specialist), or without any supervision and simply used by the individual alone. The products may also be provided by an educator (e.g., for students) or by an employer to employees (e.g., to enhance the multitasking abilities of the employee).

The present invention can incorporated into a software or computer program (e.g. a video game). The present invention can be the sole focus of the video game, such as a video game centered around navigating an object through a course while processing various interferences. Alternatively, the present invention can be incorporated into an existing game, serving as a specific portion of the game but not the the primary focus (e.g., one portion in time or space, a goal of a level, or as an intermittent task within or between levels, or as presented sparingly throughout gameplay).

In another example, the present invention is incorporated into experiences, such as a movie, television program, or an application in a social network. Progress or success in carrying out the methods can "unlock" features of this experience, or progress in participation of the separate experience. For example, when watching a movie, the present invention may appear as a game, and a user that attains a certain level of success can continue the movie. As for a social network experience, success at a certain level may contribute to unlocking certain contacts within the social network. Integration into a social network may be done with programs such as FACEBOOK®, TWITTER®, LINKED-IN®, GOOGLE PLUS® and others known to one in the art.

Alternatively, the present invention is incorporated into a non-electronic game that the individual plays, such as a board game, a card game, or an interpersonal/social game. In such a game, interferences may be tangible portions of the game (e.g. a specific type of cards) or may be actions deriving from game rules (e.g., a second gameplayer distracting or interrupting a first gameplayer who is accomplishing the training).

The present invention can also be incorporated into a cognitive laboratory-style paradigm or cognitive training task, analogous in substance and execution to those known in the art and practiced by cognitive science researchers, such as the n-back working memory task and the Sustained Attention to Response Task (SART), details of which are known in the art. These and other paradigms may be used for research purposes, or for training of an individual.

In an additional example, the task in the methods of the present disclosure can be an actual real-world task that is part of the individual's daily life. The individual may desire training on this particular task. Distractions or interruptions are then administered to the individual via a game, a software, or an interface that at a given frequency during the task. The individual can decide when to do the task that they would desire training on, and then activate the distraction/interruption product employing the methods of the present invention. The individual is then being rigorously trained to do the task in the presence of interference. The individual may provide the feedback on success at completing the task, time to complete the task, or general satisfaction with the product of the task. The feedback from the individual would be an input to the interference interface. As a non-limiting example, a distraction/interruption application can be developed for a mobile device (e.g., iPhone®) that includes a variety of distractions and interruptions. A user may, for instance, want to improve their working memory while typing a report for work, and would therefore activate the distraction/interruption application when commencing the work report. The distraction/interruption application receives and registers input from responses and non-responses, as well as updates on the individual's progress on his task. The analysis can be reported either from an objective (e.g. percent completed) or subjective (e.g. satisfaction with progress) measure. The distraction/interruption application can increase difficulty on the distraction/interruption stimuli as described above, as well as increase "difficulty" on the task by, for example, requiring a faster pace (in % of task completed per time).

The products provided herein also encompass diagnostics methods described above. Any of the products described above can be used as an "assessment" or "diagnostic" in which an individual engages for a defined period of time on the method. An evaluator then determines that individual's cognitive impairment or susceptibility to interferences. Any types of interference described herein can be applied in a product to hone in on the exact deficit or susceptibility of that individual. This diagnostic product can generate a report of one's deficit features, and optionally, a recommended training regimen to enhancement of those corresponding skills.

Computer System and Tools

The present invention provides computer program products that, when executed on a programmable computer such as that described above with reference to FIG. 1A, can carry out the present invention. As discussed above, the subject matter described herein may be embodied in systems, apparatus, methods, and/or articles depending on the desired configuration. In particular, various implementations of the subject methods described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g. video camera, microphone, joystick, keyboard, and/or mouse), and at least one output device (e.g. speaker, headphones, and/or monitor display). Other input devices include those employed in physical exercise, such as a treadmill, elliptical, bicycle, steppers, motion/position sensor remotes (e.g. Wii), etc.

These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal.

Similarly, systems of the present invention may also include a processor, such as CPUs, and a memory coupled to the processor. The system further includes a user interface (e.g. GUI) and one or more communication buses for interconnecting these components. The user interface includes at least one or more actuators (e.g. display or speakers) and one or more sensors, and may also include one or more feedback devices. For example, speakers or headphones may provide auditory prompting and feedback to the individual during execution of the computer program. Input devices such as a joystick, a mouse, a keyboard, or a device with motion/position sensor technology (e.g. Wii remote) allow the individual to navigate the computer program, and to select particular responses after visual or auditory prompting by the computer program. Where the methods involve physical exercise as an input or part of the regimen, the input can further employ exercise machines, such as a treadmill, bicycle, stepper, Wii Fit, and the like.

The memory may include one or more programs that cause the processor to perform one or more of the operations of the methods described herein. Memory may include high speed random access memory and may also include non-volatile memory, such as one or more magnetic disk storage devices. Memory may include mass storage that is remotely located from the central processing unit(s). The memory stores an operating system (e.g., Microsoft Windows, Linux or UNIX), an application module, and may optionally store a network communication module. Although a number of different computer platforms are applicable to the present disclosure, embodiments of the present disclosure execute on either IBM compatible computers or Apple computers, or similarly configured computing devices such as set top boxes, handheld devices (e.g. personal digital assistants (PDAs), mobile devices, smart phones, tablets), gaining consoles, etc.

As noted above, the system may optionally include one or more networks or other communications interfaces, such as a network interface for conveying testing or training results to another system or device. The computer network contains computers, similar to the one described above, connected to a server. The connection between the computers and the server can be made via a local area network (LAN), a wide area network (WAN), or via modem connections, directly or through the Internet. A printer may also be connected to the computer in a network to illustrate that an individual can print out reports associated with the computer program of the present disclosure. The computer network allows information such as test scores, game statistics, and other data pertaining to an individual's performance to flow from one computer to another, e.g. a server. Data pertaining to an individual's performance can include, fore example, reaction time, response variance, correct hits, omission errors, false alarms, learning rate, and/or performance threshold, etc. An administrator can review the information and can then download configuration and data pertaining to a particular individual, back to the individual's computer. Alternatively, or additionally, the server may execute the computer program, and the individual may interact with the program via the individual's computer, e.g., in a client/server relationship.

As noted above, the individual may perform the training exercise via a graphical user interface (GUI), whereby graphical elements and/or sounds are presented to the individual and whereby the individual may provide responses.

For example, the GUI may include the visual field within which various images, e.g., target stimulus, may be displayed in a sequence to the individual, as well as various on-screen buttons or controls whereby the individual may interact with the training exercise. For example, the display may provide a start button in which the individual may press (e.g., click on) to begin or resume a training session. Additional GUI elements may also be provided, e.g., for indicating various aspects of the individual's progress or status with respect to the exercise or task, such as the difficulty level of the current training block. Examples include a bonus meter (or equivalent), which may indicate the number of correct responses in a row, a graphical element that flashes, a program that plays music, and/or award bonus points, when some specified number, e.g., 5, of correct responses is attained.

The application module executing the present invention may include one or more of the following: a) a stimuli generation control program, module or instructions, for generating series of stimuli, as described above for the present method; b) an actuator or display control program, module, or instructions, for producing or presenting the stimuli to an individual; c) a sensor control program, module or instructions for receiving input by extracting raw data in the sensor signals indicative of the individual's response; the sensor control program, module or instructions may also include instructions for controlling operation of the one or more sensors; d) a measurement analysis program, module or instructions, for analyzing the individual's responses to produce measurements and analyses, as discussed above; and e) a feedback program, module or instructions, for generating feedback signals as output for presentation to the individual via the one or more actuators or feedback devices.

The application module may furthermore store data, which includes the measurement data for an individual, and optionally may also include analysis results and the like. The application module may also store data derived from theoretical users or actual users other than the individual. Such data may be used as normative data from one or more control groups of individuals, and optionally may also include analysis results, and the like, based on the measurement data from the one or more control groups. Any of the programs described above may be stored or executed from more than one locations, e.g. more than one computer readable medium. For example, the stimuli generation program may be executed remotely via a network while the measurement analysis program may be stored and/or executed locally.

As noted above, the methods of the present disclosure can be employed as computer-based exercises and tasks in order to improve an individual's cognition. e.g., the efficiency and capacity of performing a task in the presence of an interference. Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results.

The following examples further illustrate the present invention and should not be construed as in any way limiting its scope.

Use of Methods and Tools in Conjunction with Other Therapeutics and Diagnostics

The methods described in this application can be used with other interventions which are known to improve cognition, increase multitasking abilities, improve mood and treat diseases and conditions. Interventions include both drugs as well as cognitive training and psychotherapeutic techniques. Sessions and training programs may be used either consequentively or simultaneously with the interventions. When used consequentively, the sessions and training programs can be used either prior to the other intervention or after the other intervention. The sessions and training programs may be used with one or multiple interventions.

Drug therapies include, but are not limited to cholinesterase inhibitors, memanatine, anti-depressants (e.g., selective serotonin-reuptake inhibitors, norepinephrine reuptake inhibitors, monoamine oxidase inhibitors), anxiolytics (e.g., benzodiazepines, buspirone, barbiturates) and antipsyhotics.

Cognitive training techniques include, but are not limited to computerized cognitive training, cognitive-behavioral training, cognitive remediation therapy, speech therapy.

Psychotherapeutic techniques include, but are not limited to, behavior therapy, cognitive therapy, psychodynamic therapy, psychoanalytic therapy, group therapy, family counseling, art therapy, music therapy, vocational therapy, humanistic therapy, existential therapy, transpersonal therapy, client-centered therapy (also called person-centered therapy), Gestalt therapy, biofeedback therapy, rational emotive behavioral therapy, reality therapy, response based therapy, Sandplay therapy, status dynamics therapy, hypnosis and validation therapy. It is further understood that psychotherapy may involve combining two or more techniques and that a therapist can select and adjust the techniques based on the needs of the individual patient and the patient's response.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1 Experimental Setup for Assessment

The study involved adults at various ages (recruited into 4 randomized study groups: 1) single-task training, 2) multitasking training, 3) distraction training, and 3) no-contact control (NCC). Training groups engaged in 12 hours of home training and 6 laboratory visits: 1) neuropsychological testing, 2 & 3) pre- and post-training cognitive assessment, 4 & 5) pre- and post-training neural assessment, and 6) six-month follow-up cognitive evaluation. NCC group engages in 1) neuropsychological testing, 2 & 3) pre- and post-no-contact interval cognitive assessment, 4 & 5) pre- and neural assessment.

To evaluate interference abilities pre- and post-training, participants engage in five experimental tasks from three categories:

single tasks (1) target discrimination—"shoot", (2) visuo-motor tracking—"drive";

distraction tasks (3) target discrimination while passively exposed to tracking task-"shoot with road" (4) visuomotor tracking while passively exposed to target discrimination task—"drive with signs"); and interruption/multitasking (5) simultaneous target discrimination and visuomotor tracking—"shoot with road").

There are three, 5-minute blocks of each task, presented in a pseudo-randomized order across participants.

1) Single Task: Target Discrimination ("Shoot").

In this task, a "sign" appears on a black background, 2.5 degrees above a central fixation cross at a randomized SOA (stimulus onset asynchrony: 2, 2.5, and 3 sec). An example of a screen shot is shown left of panel in FIG. 1B. Prior to the experiment, participants were informed of a colored shape that was the target sign (e.g., green circle). A button press was to be made (with left forefinger) to all target signs, but not to non-target signs, which can differ in either color or shape. A hit on a target sign, indicated by the fixation cross turning green, occurred if the response was made within a pre-defined time window. This time window was established prior to the experiment using a staircase thresholding procedure that individually determined the window duration that resulted in discrimination task performance of 80% accuracy. Details on the thresholding procedures are discussed incojunction with below Example 5. 33.3% of the signs were targets, 33.3%; were contingent, non-target signs (share the color dimension) and 33.3% were non-contingent, non-target signs (share no feature). Recorded behavioral data included: hits, misses, correct rejections, false positives and response times. Participants received accuracy feedback at the end of each run.

2) Single Task: Visuomotor Tracking ("Drive").

Figure 1C:
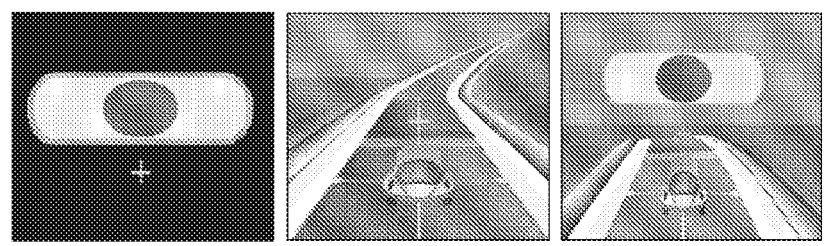
FIG. 1C illustrates pictorial representations of a single task involving target discrimination without interference (left), a visual-motor tracking without interference (middle), and multi-tasking involving both target discrimination and visual-motor tracking (right) in accordance with illustrated embodiments of the present invention.

Participants viewed a three-dimensional environment with a road extending into the distance. They saw their "car" positioned on a road, 2.5 degrees below a central fixation cross. An example of a screen shot is shown in FIGS. 1B and 1C. When the session began, the car would appear to move forward as the road advanced towards the participant. As the road advanced, it curved to the left and right, and participants were instructed to maintain the car in the center of the road (gray zone) using the horizontal axis of the joystick with their right hand, all the while maintaining visual fixation on the cross hair. In addition to the road turning, it was also graded. Participants maintained constant speed by keeping the car within an indicator (speedometer) that advanced on the road along with the car. This was accomplished by using the vertical axis of the joystick to correct for speed changes resulting from hills and valleys; i.e., pushing forward when going up a hill to speed up and pulling back when going down a hill to slow down. The speed of the car was pre-established for each participant prior to each session using a staircase thresholding procedure to attain a performance level of 80% time on road. The exact position on the road relative to center was recorded. Feedback to participants for deviations from the road was indicated by shaking of the crosshair when off road, and overall time on road was presented at the end of each block.

3) Distraction Task: Target Discrimination while Passively Exposed to Tracking Task ("Shoot with Road").

In this task, participants performed the target discrimination task exactly as described above, but the road was presented as the background, as opposed to the black field used in the single tasks. An example of a screen shot is shown in FIG. 1B. Also, the car advanced along the road on "auto-pilot." There was no goal to attend to the road or car, it was presented solely as a potential distractor to target discrimination.

4) Distraction Task: Visuomotor Tracking while Passively Exposed to Target Discrimination Task ("Drive with Signs").

This task was the mirror version of the other distraction task. Here the goal was to perform visuomotor tracking ("car driving"), while irrelevant visual signs were presented as potential distractors. An example of a screen shot would be similar to the screen shot in distraction task described immediately above.

5) Interruption Task/Multitasking: Simultaneous Target Discrimination and Visuomotor Tracking ("Shoot & Drive").

The participant performed both single-tasks at the same time. An example of a screen shot would be similar to the screen shot in distraction task described immediately above. Note that there was both perceptual and motor overlap between the two tasks.

Example 2 Training

There were two types of interference training (distraction training and multitasking training), one active control group (single-task training) and a no-contact control group (NCC), which except for the NCC engaged in 12 one-hour training sessions over a 4-week period at their homes. Single-task training involved a randomized alternation between the two single tasks described in the interference assessment section: target discrimination tasks and visuomotor tracking tasks were presented in 3-minute blocks. Comparably, distraction training involved a randomized alternation of the two distraction tasks. Multitasking training will involve 12 sessions of simultaneous target discrimination and visuomotor tracking. Task difficulty at the start of the first session was individually customized based on single-task levels obtained via the thresholding procedure during the preceding lab visit (i.e., road speed and target discrimination response window optimized to result in 80% performance levels on single tasks alone). A major distinction between the training sessions and the neural assessment tasks was that training was adaptive, such that as performance improved, task difficulty increased to maintain constant accuracy (i.e., discrimination time window decreases and road speed increases). Each session was linked such the next session starts at the level attained at the end of the previous session. There were three types of feedback: 1) Real-time feedback—color changes in the fixation crosshair (discrimination task) and shaking of the crosshair (tracking task). 2) Punctuated feedback—the 'level' that corresponds to discrimination window time and road speed, attained at the end of each run is reported. For multitasking training, there was also feedback on the combined performance of each task, presented as the "overall level." This reflected the lower performing task and so, it encouraged attention to both tasks. 3) At the end of a session, the final session level was reported, as well as a map to visualize where they had "traveled" along this 12-part mountain course. This was included to increase compliance in the entire 12 session training regimen.

All participants trained at home using laptops and joysticks. At the start of the training period, a person familiar with the experiments presented herein visited participants at home to help set up the computer and to instruct on training. There was also an instruction movie that reinforced the instructions and goals at the launch of each session. Telephone and email support were provided to participants throughout their involvement and they received weekly email reminders and two check-in phone calls. Participants were allowed to set their own training schedule, but were instructed to complete three sessions each week in a distraction-free environment, e.g. without alcohol consumption prior to or during training. During each session, a full set of performance data was recorded on the laptops, so that compliance with protocol was monitored and learning curves were plotted over the training period. In addition, the laptop video camera immediately above the center of the screen was activated at the start each session (indicated by a green light), allowing a visual assessment of the task engagement, as well as motivating participants to be compliant with instructions. Both performance and video data were automatically potted to a secure lab server using a pre-established Dropbox account for those participants with internet connections.

Example 3 Behavioral Assessment with Interference

Figure 2:
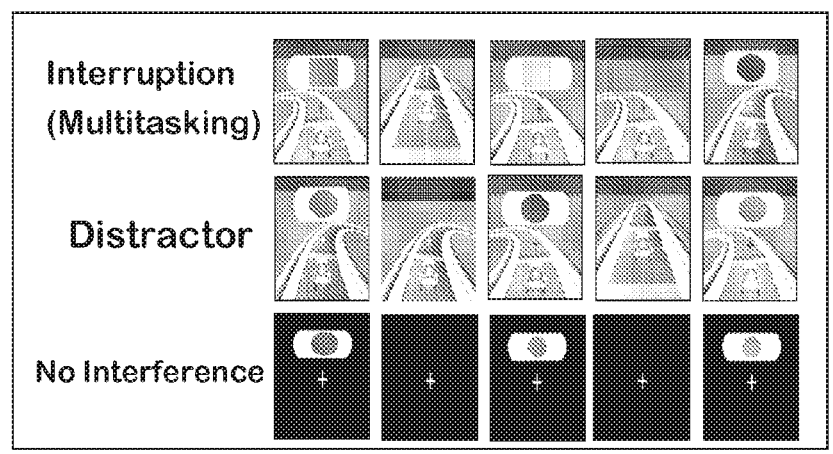
FIG. 2 illustrates pictorial representations of various combinations of tasks and different interferences in accordance with illustrated embodiments of the present invention.
Figure 3:
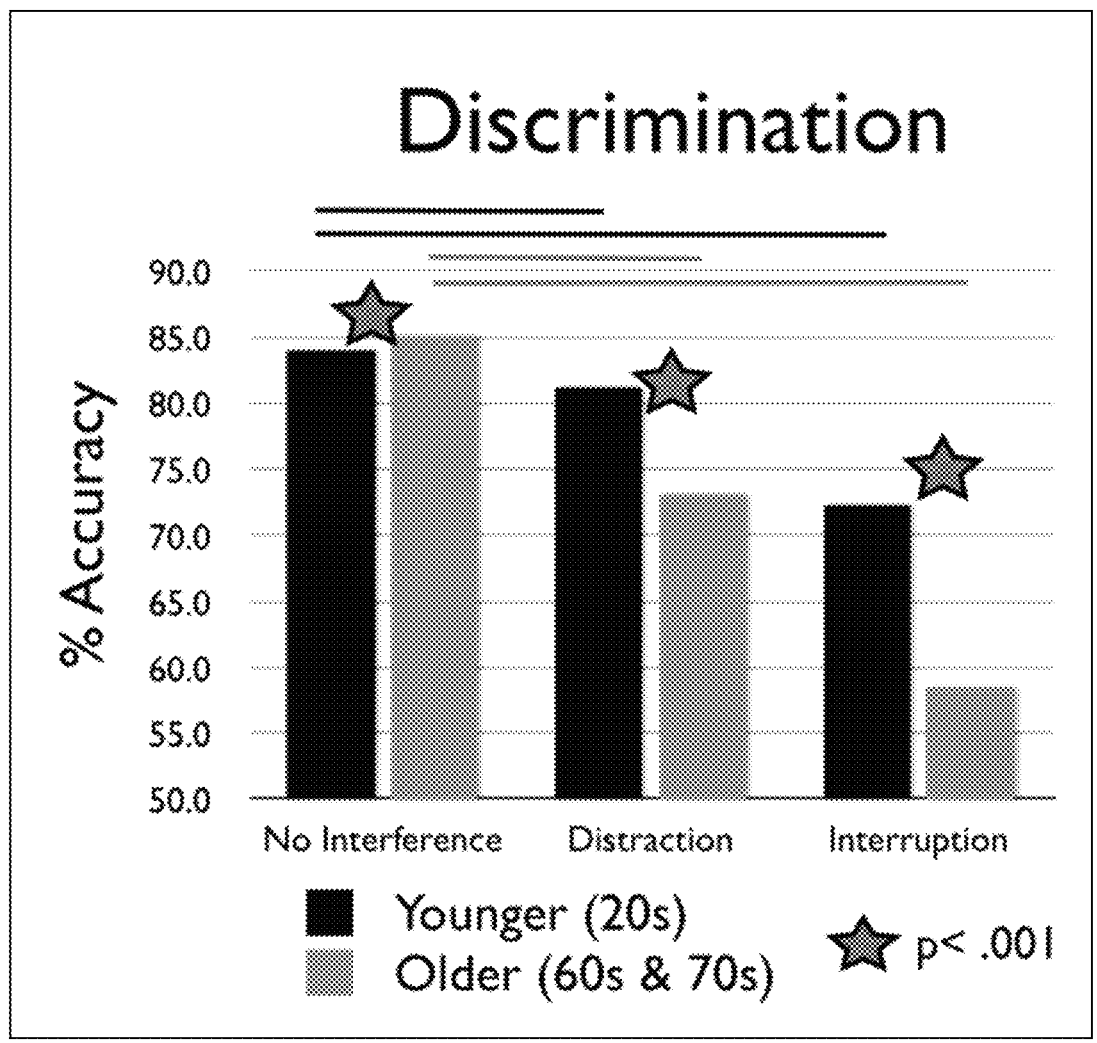
FIG. 3 illustrates a graph representing behavioral assessment of experimental subjects who participated in the tasks and/or interferences represented in FIG. 2 in accordance with illustrated embodiments of the present invention.

A behavioral assessment of interference effects in younger (20s) and older adults (e.g. 60-80 years of age) revealed significant distraction and interruption costs both within and between age groups versus the no interference condition. This was seen in the primary task of target discrimination (FIGS. 2, 3). The same finding was observed for visuomotor tracking for interruption, but not distraction.

Figure 4A:
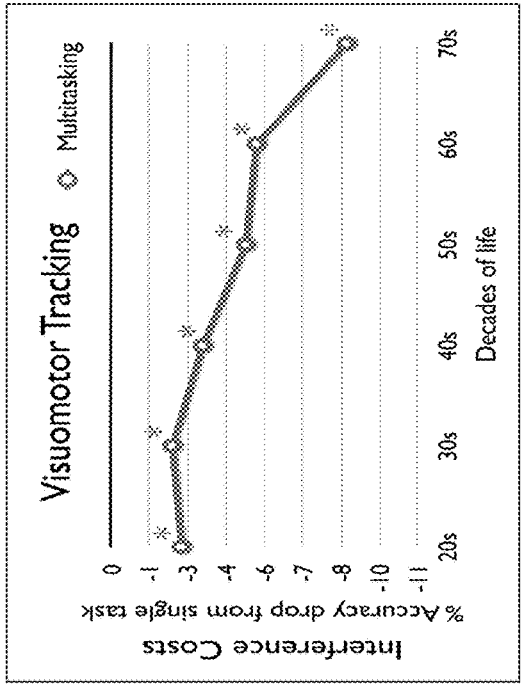
FIG. 4A illustrates a graph showing the impact on target discrimination abilities of distractors and interruptors (multitasking) in adults across the lifespan in accordance with illustrated embodiments of the present invention.
Figure 4B:
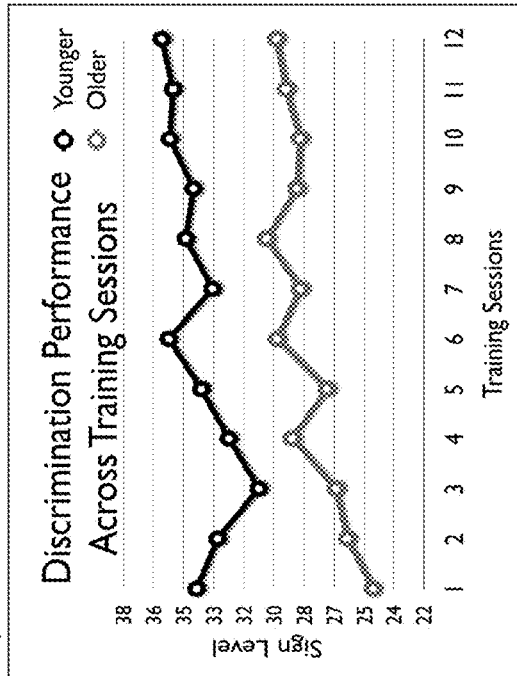
FIG. 4B illustrates a graph representing the impact on visuomotor tracking abilities of distractors and interruptors (multitasking) in adults across the lifespan in accordance with illustrated embodiments of the present invention.

An adult lifespan study of individuals (20-80 years of age) revealed a significant distraction and multitasking cost on the accuracy of target discrimination (FIG. 4A), and a significant multitasking cost on the accuracy of visuomotor tracking for each of the six decades of life studied. (FIG. 4B) No impact of distraction on tracking was observed at any age. These interference costs increased with each decade of life and a significant increase in all interference costs were observed between groups of younger and older adults, as classified in the proposed study. This preliminary study and the significant findings are critical, as it motivates the use of a training regimen to remediate these interference costs.

Figure 5A:
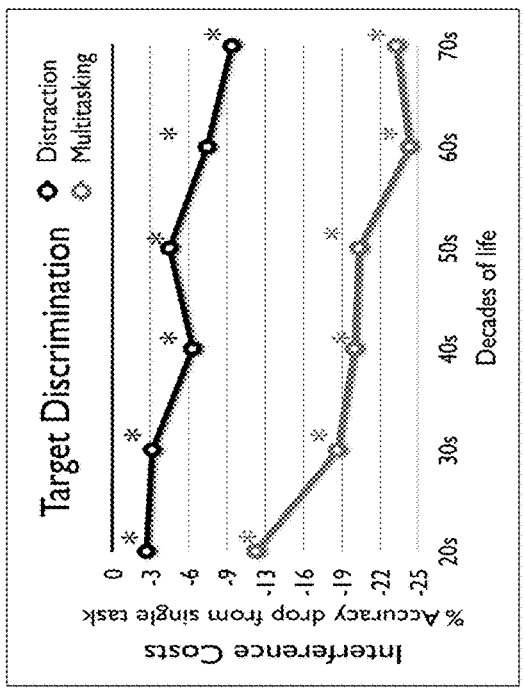
FIG. 5A illustrates a graph showing tracking performance in the setting of interruption for younger adults (dark line) and older adults (gray line) across 12 training sessions in accordance with illustrated embodiments of the present invention
Figure 5B:
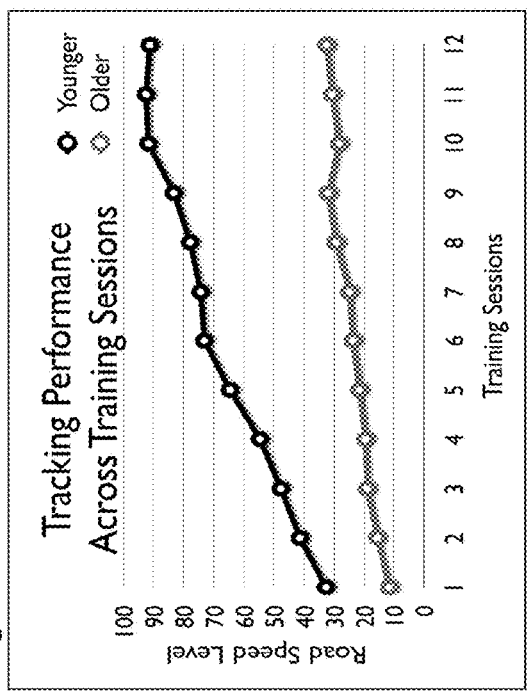
FIG. 5B illustrates a graph showing discrimination performance in the setting of interruption for younger adults (dark line) and older adults (gray line) across 12 training sessions in accordance with illustrated embodiments of the present invention.

Example 4 Effects of Training 5 younger and 5 older adults participated in 12 one-hour sessions of multitasking training on laptops at home. This pilot study fine-tuned an illustrative embodiment of methods of the present invention. Examination of the data from the training sessions revealed consistent improvement across sessions for tracking in every younger and older participant (FIG. 5A; group data). Of note, there was a distinctly reduced learning slope for older participants. Discrimination performance also improved across sessions in all but two of the participants. The learning curve was more variable across sessions for this performance measure. A completed auditory distraction training also revealed the same pattern of learning shown here in younger and older adults.

Figure 6:
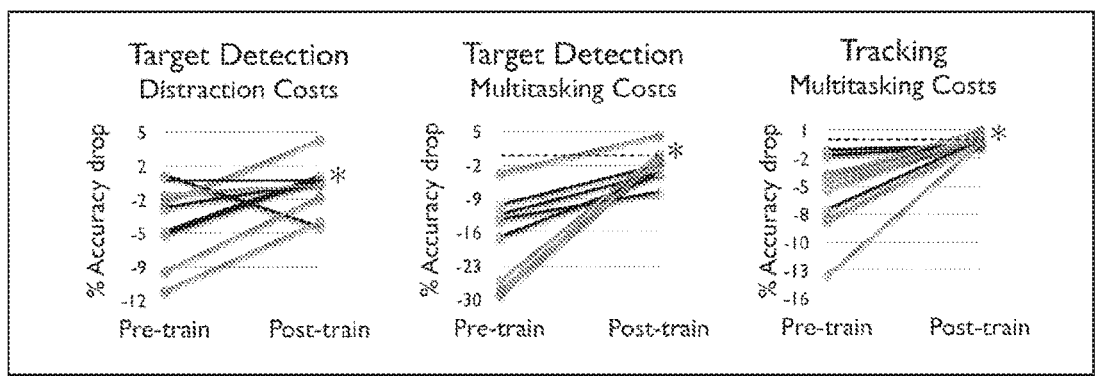
FIG. 6 illustrates pre- and post-training performance of target detection in the presence of distractors (distraction costs) or in the presence of interruptors (multitasking costs), and pre- and post-training performance of visuomotor tracking in the presence of interruptors (multitasking costs) in accordance with illustrated embodiments of the present invention.

Pre- and post-training evaluation performed in the laboratory revealed that for target discrimination, both distraction (FIG. 6; left) and multitasking (FIG. 6; middle) costs were reduced in all younger (black) and older (gray) adults, except one. For tracking, every individual resolved multitasking costs (FIG. 6; right). Dashed line and asterisks designate the level at which there was no interference cost.

Figure 7:
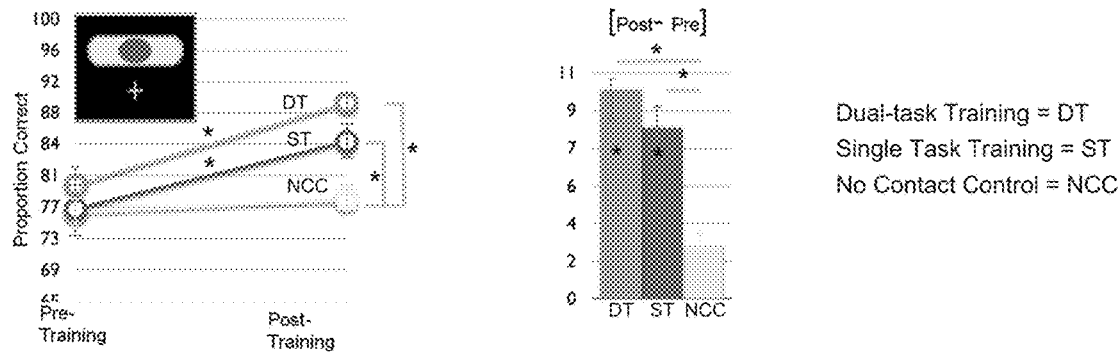
FIG. 7 illustrates pre- and post-training group-averaged analysis of target detection in a multitasking interference group (Dual-task) compared to a task-alone control (Single-Task Training) and a practice-effect control group (No Contact Control) in accordance with illustrated embodiments of the present invention (Panel A—Single Task Performance; Panel B—Dual Task Performance; Panel C—Dual-task Cost)
Figure 7:
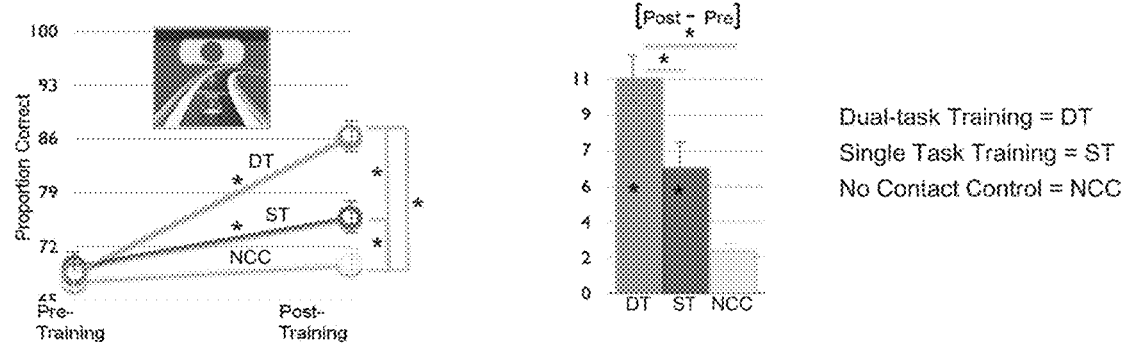
Figure 7:
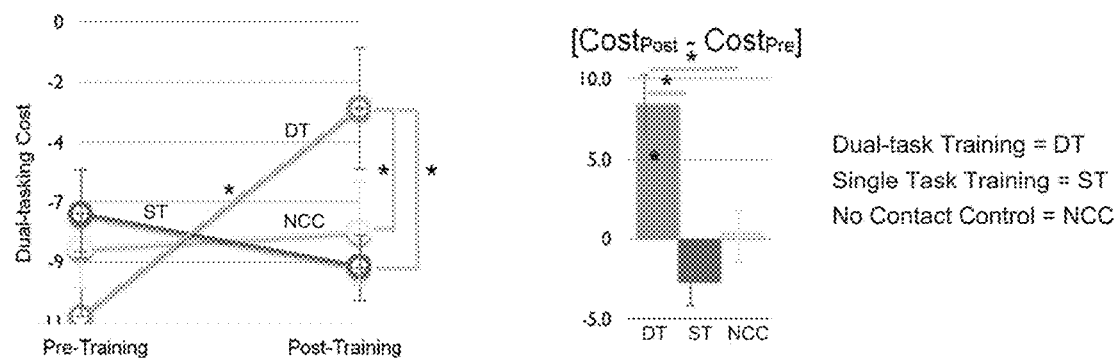

FIG. 7 further demonstrates the beneficial effects of interference training. Separating the data between those that received interference training (Dual-task) and those that received task-alone training (Single-task) and averaging within groups showed that participants who received interference training in the form of multitasking (Dual-task group) outperform the no-interference training group (Single-task) and control groups in terms at a multitasking test (FIG. 7. Panle Bapplied test is in the graph inset). Single task performance (FIG. 7, Panel A) is helped to similar degrees by single task and dulat task training, and only that Dual-task group was able to remove their interference cost, despite the fact that the single-task group performed many hours excelling at each individual task (FIG. 7, Panel C).

Figure 8:
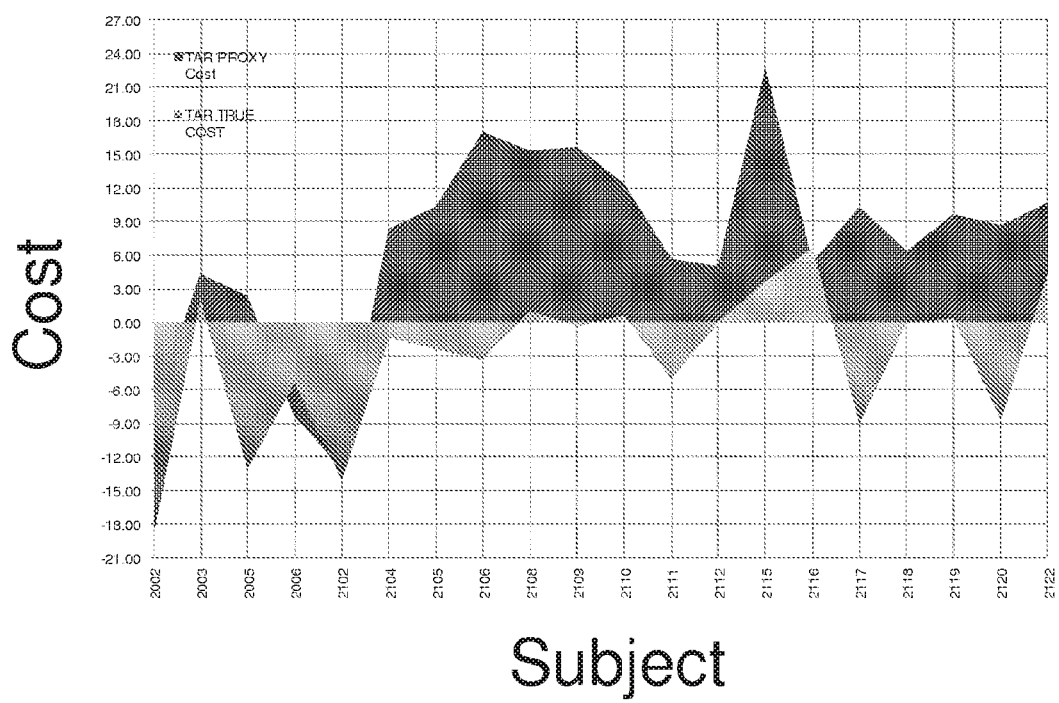
FIG. 8 is a post-training analysis depicting resolution of interference cost as measured by two different methods in accordance with illustrated embodiments of the present invention.

Interference cost was directly measured by instructing individuals, before and after their training program, to perform an assessment of their targeting task as in FIG. 11. A "true" cost resolution was first assessed, in the sense that participants' targeting performance was compared with and without interference both post-training. Therefore, a cost resolution would be a positive number or small negative number (multitasking interference cost in most cases pre-training was on the order of 10% or greater). FIG. 8 shows that, giving a buffer of 3% as the minimum to determine that interference cost has been resolved, 13 out of the 20 participants resolved their interference cost. However, instead of requiring participants to take a full assessment post-training, it is possible to assess their post-training targeting performance with interference compared to their pre-training targeting performance without interference. This allows the potential for false positives where participants' might have simply increased their targeting performance very highly without resolving interference cost. However, it is shown in FIG. 8 that such a "proxy" measure can detect all of those participants who resolved their true cost (true positives). While there were 4 false positives, the proxy approach demonstrates a more streamlined way to approximate the assessment of cost resolution if a less time-intensive post-training assessment process is desired.

Transfer of benefit, or the ability to demonstrate beneficial effects on functions outside of the specific task that was trained, is important to indicate real-world utility and potential target population utility of any cognitive training program. Pre- and post-training assessments of transfer of benefit were also experimentally tested for each subject. The tests were: Change Detection Task for visual working memory capacity, AID for visual working memory, Filter Task for visual working memory, Auditory Consonant Trigrams (ACT) for verbal working memory, Stroop test for inhibition processing, PRP Dual Task for multitasking, Conversational interruption for multimodal multitasking, Predictive Task Switching for task switching, Tests of Variables of Attention (TOVA) for sustained attention and impulsivity. MOT for visual attention capacity, useful Field of View (uFOV) for selective and divided attention and speed of processing, tlADL for functional outcomes, WAIS Digit Symbol for speed of processing, and a Detection Reaction Time task for simple reaction time. Multiple improvements were seen on this battery of tests that indicate a transfer of benefit to tasks that are distinct from the task that was trained.

Figure 9:
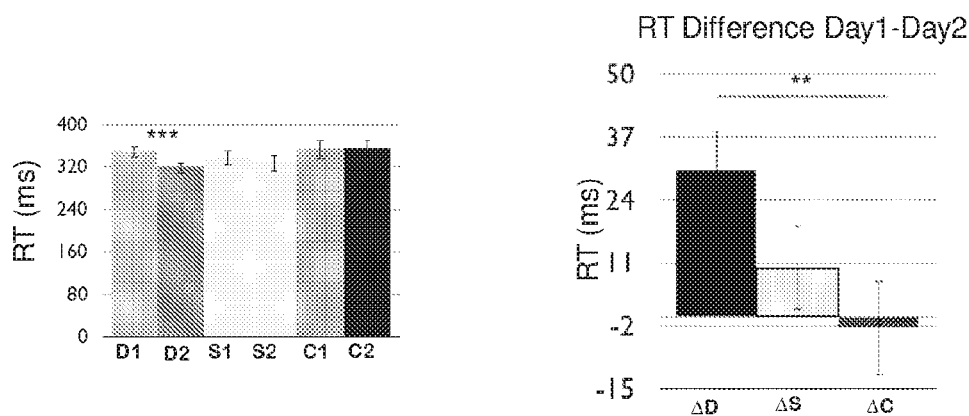
FIG. 9 illustrates results of a pre-training and post-training assessment for an exemplary task in accordance with illustrated embodiments of the present invention.
Figure 9:
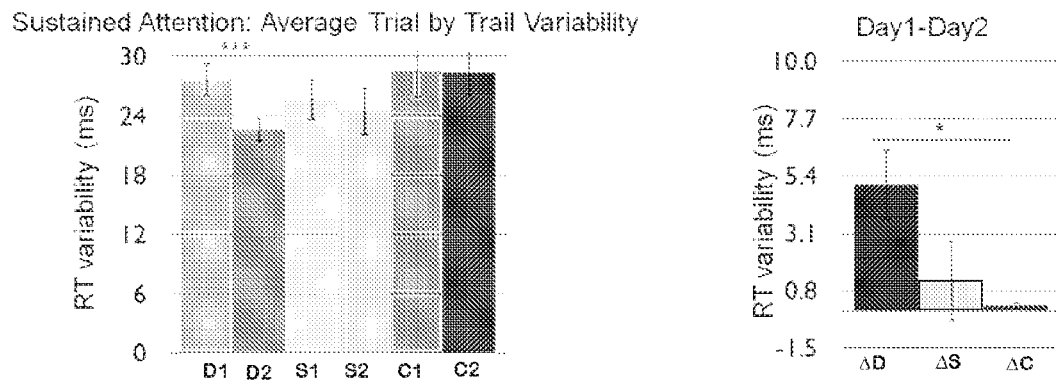
Figure 9:
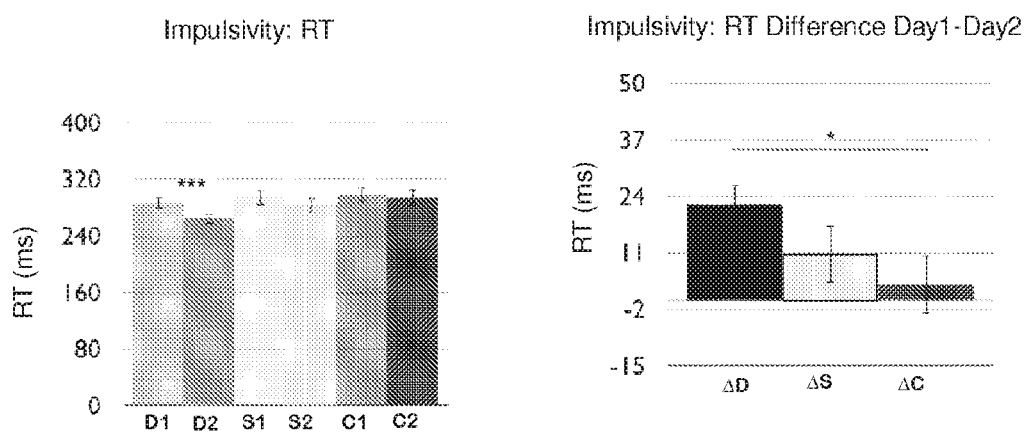

An example of results of the TOVA test is shown in FIG. 9. Compared to a group that did not receive active training (Control for test-retest practice effects) and a group that received only the single task training, i.e. no interference (Single), the group receiving the task plus multitasking interference training (Dual) showed improvement and faster responses on a sustained attention task (FIG. 9, Panel A), less variability in response times in a sustained attention task (FIG. 9, Panel B), and faster responses with no decrement in accuracy on an impulsivity task (FIG. 9, Panel C). Since the TOVA assessment is used by clinicians in the diagnosis and maintenance of attention deficit-hyperactivity disorder (ADHD), these data highlight an example where a transfer of benefit study can signal importance for a healthy population (sustained attention and impulsivity) and a clinical population (ADHD).

Additional results of transfer of benefit include measurable changes in the PRP Dual Task multitasking paradigm, in which participants on interference training improved to respond faster and with greater accuracy than control groups; and in a Face Discrimination working memory paradigm adapted from the Gazzaley lab, where participants improved to a greater degree than control groups at faster reaction times to both an attended target and in the face of distracting target.

Example 5 Thresholding

The objective of the thresholding algorithm was to achieve as close to about 80% performance in the visuomotor tracking task and/or target discrimination (or target detection) task from the individual by adjusting the difficulty levels appropriately. In a visuomotor tracking task that involved navigating a vehicle on a road (road trial): Increments in difficulty entailed: 1.) a higher perceived road speed, 2.) more momentum by the car (requiring larger corrections) and 3.) faster transitions between road pieces requiring quicker responses (resulting from the higher speed). In a target discrimination task (sign task), increments in sign difficulty entailed a smaller reaction time window to respond to a target stimulus. The algorithm involved in determining a difficulty level employed a combination of staircase thresholding and linear extrapolation over a series of 12 one-minute road trials and 9 two-minute sign trials. Depending on the individual's performance on the previous trial, the difficulty was linearly incremented (if above 80%) or decremented (if below 80%) or held constant (if they performed at 80%). After the completion of all thresholding steps, a difficulty level was calculated by an averaged linear extrapolation for 80% performance ignoring the first three trials (for purposes of giving the individual some familiarity). This procedure was done for the road task and sign task separately yielding two individual scores for that participating individual. As noted above, other percentages of accuracy other than 80% can also be used.

The training program, which involved the practice of a combined road and sign task took place at the individual's own home for multiple sessions. How difficulty levels were changed was based on the staircase algorithm described above to adaptively change the road and sign difficulty. Following each three-minute trials, the road and sign difficulty level was linearly adjusted based on the sign and road performance of the previous run. Both difficulty levels were increased only when the participant performed over 80% on signs and road. They were both decreased only when the participant performed below 80% on both objectives. In all other cases, no adjustments were made and the difficulty levels stayed the same for the next run. The difficulty levels the participant ended on were used for the first trial of the next session.

Example 6 Interference. Re-Interference Training

In an attempt to have a long-term, sustainable training program that can challenge all participants, a training program was constructed and a study conducted similar to the one discussed in the examples above, but that instead of using a single type of interference and adapting difficulty within that paradigm, is designed to layer on increasing interference challenges as participants train. The determination of when new, more complex challenges are applied to the training program and presented to the user was based on determination of when they had minimized or removed their interference cost (difference between the goal task and the goal task+interference).

The study involved healthy adults at various ages (recruited into 4 randomized study groups: 1) proprietary interference training constructed as described in the present invention, 2) non-contact control, and 3) control training in the form of a commercial video game. The two training groups engaged in 10 hours of home training, and all groups had 2 laboratory visits for pre- and post-training neural assessment.

The training program consisted of a computerized game environment on a mobile platform. The computerized program first performed a threshold on the participant to determine their 80% accuracy level on the first interference challenge: targeting (tapping the mobile device) any objects that appeared on the screen, while navigating (tilting the mobile device) through a non-linear course. Before the training session was initiated, interference cost on this challenge was determined in a pre-training assessment. The participants then trained on the dual-task environment, which adapted to their performance by increasing or decreasing the time-domain requirements for targeting and navigating. Either at a set time interval of 5 runs, or sooner at the participant's election, an assessment was performed again in the game environment to determine interference cost. The data was sent to a remote server and compared against the first pre-training assessment, analyzing change in interference cost. Where the interference cost was determined to have not been minimized (by a pre-set value), the game entered the player back into the training session on the same interference challenge. Where the interference cost was determined to have been minimized, the game entered the player into a new pre-training assessment, this time on a pre-defined new interference that was more complex than the first a targeting discrimination task (tapping targets only with specific features) while still navigating through a non-linear course.

That process repeated for all participants, eventually taking high performers through multiple challenges (including discrimination tasks, complex navigation tasks, and more visual elements on the screen). The end result was a training program experience that was customized for the participant through a limited set of interference challenges, based on their resolution of interference cost for each interference challenge. At any point in time, remote data servers analyzed the incoming data and directed the computerized program to place the participant in one of two paths (the current task with interference or a new task with interference) as opposed to a pre-defined training progression.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A computer-implemented method for altering a cognitive skill measurement program for an individual using a computer device having a display component and an input device, the method comprising:

using one or more computer processors to execute instructions stored in one or more memory storage devices comprising computer executable instructions to perform operations including:
  delivering the cognitive skill measurement program to the individual, the cognitive skill measurement program comprising:
    presenting a first task to the individual using the display component requiring a first response from the individual via the input device, wherein the input device comprises a motion or position sensor, exercise equipment, or both, and
    presenting a first interference with the first task, the first task requiring a second response from the individual to the first task in the presence of an interference via the input device, wherein the first interference diverts the individual's attention from the first task and is selected from the group consisting of a distraction and an interruptor; and
    receiving data corresponding to the individual's first response and second response, wherein the computer device is configured to use the input device to measure data indicative of physical actions of the individual to obtain the first response and/or the second response; and
  altering a parameter of the cognitive skill measurement program based on the received data.

2. The method of claim 1, wherein the data is collected with an application module residing on the computer device.

3. The method of claim 2, wherein additional data derived from at least one of theoretical individuals and actual individuals is stored in the application module.

4. The method of claim 2, wherein the application module further comprises a database for storing either or both of the received data and values of the parameters of the cognitive skill measurement program.

5. The method of claim 4, wherein the database further comprises received data from a plurality of other individuals.

6. The method of claim 1, wherein the cognitive skill measurement program is delivered to the individual on the computer device and the data is received at a server remote from the computer device.

7. The method of claim 6, wherein additional data derived from at least one of theoretical individuals and actual individuals is stored on the remote server.

8. The method of claim 1, wherein the data comprises at least one of reaction time, response variance, correct hits, omission errors, false alarms, learning rate, and performance threshold.

9. The method of claim 1, further comprising: analyzing the difference in the individual's performance when performing the first task without interference and with interference by determining a difference between the first and second responses to determine an individual's cognitive ability.

10. The method of claim 1, wherein the parameter is selected from the group consisting of: type of task, type of interference, duration of the interference, and timing of the interference.

11. The method of claim 1, wherein the first task is a continuous visuo-motor tracking task.

12. The method of claim 1, wherein the first interference is a target discrimination interference.

13. The method of claim 1, wherein one or more of the first task and the first interference comprises a human face, a face of a specific age range, a nonhuman face, or any parametric variation of a face.

14. The method of claim 1, wherein the computer device is selected from the group consisting of a desktop computer, a laptop computer, a computer tablet device, a smart phone device and a video game device.

15. The method of claim 1, wherein the computer device comprises one or more peripheral devices.

16. A system for altering a cognitive skill measurement program for an individual, the system comprising:
  computer-executable instructions stored on physical memory, that when executed by one or more processors, perform operations comprising:
    delivering the cognitive skill measurement program to the individual, the cognitive skill measurement program comprising:
      presenting a first task to the individual using a display component requiring a first response from the individual via an input device, wherein the input device comprises a motion or position sensor, exercise equipment, or both, and
      presenting a first interference with the first task, the first task requiring a second response from the individual to the first task in the presence of an interference via the input device, wherein the first interference diverts the individual's attention from the first task and is selected from the group consisting of a distraction and an interruptor; and
      receiving data corresponding to the individual's first and second responses, wherein the computer device is configured to use the input device to measure data indicative of physical actions of the individual to obtain the first response and/or the second response; and
    altering a parameter of the cognitive skill measurement program based on the received data.

17. The system of claim 16, wherein the data comprises at least one of reaction time, response variance, correct hits, omission errors, false alarms, learning rate, and performance threshold.

18. The system of claim 16, further comprising: analyzing the difference in the individual's performance when performing the first task without interference and with interference by determining a difference between the first and second responses to determine an individual's cognitive ability.

19. The system of claim 16, wherein the parameter is selected from the group consisting of type of task, type of interference, duration of the interference, and timing of interference.

20. The system of claim 16, wherein the first task is a continuous visuo-motor tracking task.

21. The system of claim 16, wherein the first interference is a target discrimination interference.

22. The system of claim 16, wherein one or more of the first task and the first interference comprises a human face, a face of a specific age range, a nonhuman face, or any parametric variation of a face.

23. The system of claim 16, wherein the cognitive skill measurement program comprises:
  presenting the first task and the first interference in an iterative manner; and
  receiving the data corresponding to the first response and the second response in an iterative manner.

24. The system of claim 16, wherein the cognitive skill measurement program further comprises:

analyzing the data corresponding to the first response and the second response to determine a measure of the individual's performance; and adjusting a difficulty level of either the first task or the first interference, or both the first task and the first interference, based at least in part on the measure of the individual's performance determined in the analyzing.

* * * * *